(12) United States Patent
Hall

(10) Patent No.: US 10,900,071 B2
(45) Date of Patent: Jan. 26, 2021

(54) IDENTIFICATION OF GENETIC MODIFICATIONS

(71) Applicant: WAKE FOREST UNIVERSITY HEALTH SCIENCES, Winston-Salem, NC (US)

(72) Inventor: Adam R. Hall, Winston-Salem, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 214 days.

(21) Appl. No.: 15/758,814

(22) PCT Filed: May 12, 2016

(86) PCT No.: PCT/US2016/032029
§ 371 (c)(1),
(2) Date: Mar. 9, 2018

(87) PCT Pub. No.: WO2016/183289
PCT Pub. Date: Nov. 17, 2016

(65) Prior Publication Data
US 2019/0040457 A1 Feb. 7, 2019

Related U.S. Application Data

(60) Provisional application No. 62/160,390, filed on May 12, 2015.

(51) Int. Cl.
| | | |
|---|---|---|
| C12Q 1/6827 | (2018.01) | |
| C12Q 1/6869 | (2018.01) | |
| C12Q 1/6834 | (2018.01) | |
| C12P 19/34 | (2006.01) | |
| C07H 21/04 | (2006.01) | |
| C12N 15/10 | (2006.01) | |

(52) U.S. Cl.
CPC .......... *C12Q 1/6827* (2013.01); *C07H 21/04* (2013.01); *C12N 15/1006* (2013.01); *C12P 19/34* (2013.01); *C12Q 1/6834* (2013.01); *C12Q 1/6869* (2013.01); *C12N 2310/335* (2013.01); *C12N 2310/336* (2013.01); *C12N 2310/3341* (2013.01); *C12Q 2521/301* (2013.01); *C12Q 2521/531* (2013.01); *C12Q 2525/101* (2013.01); *C12Q 2537/164* (2013.01); *C12Q 2600/118* (2013.01); *C12Y 207/07007* (2013.01); *C12Y 302/01017* (2013.01); *C12Y 302/02015* (2013.01)

(58) Field of Classification Search
None
See application file for complete search history.

(56) References Cited

U.S. PATENT DOCUMENTS

| | | | | |
|---|---|---|---|---|
| 6,048,696 A | * | 4/2000 | Hoffman | C12Q 1/701 435/18 |
| 2003/0180779 A1 | | 9/2003 | Lofton-Day | |
| 2006/0068415 A1 | | 3/2006 | Jones et al. | |
| 2013/0004956 A1 | | 1/2013 | Landers et al. | |
| 2013/0090588 A1 | | 4/2013 | Buus et al. | |
| 2014/0066837 A1 | * | 3/2014 | Moy | A61K 38/18 604/22 |
| 2014/0361995 A1 | | 12/2014 | Halim et al. | |
| 2015/0015175 A1 | | 1/2015 | Ariga et al. | |
| 2015/0299784 A1 | * | 10/2015 | Fan | C12Q 1/6874 506/4 |

FOREIGN PATENT DOCUMENTS

| | | |
|---|---|---|
| JP | 2013542730 A | 11/2013 |
| WO | 2012065043 A2 | 5/2012 |
| WO | 2013090588 A1 | 6/2013 |
| WO | 2015015175 A1 | 5/2015 |

OTHER PUBLICATIONS

Carlsen, et al. "Selective Detection and Quantification of Modified DNA With Solid State Nanopores"NAN Lett. May 29, 2014, vol. 14, pp. 5488-5492, Entire Document.
Schermerhorn, et al. "A Chemical and Kinetic Perspective on Base Excision Repair of DNA", ACC Chem Res. Mar. 19, 2014, vol. 47, pp. 1238-1246, Entire Document.
Nikiforov, et al. "Fluorogenic DNA Ligase and Base Excision Repair Enzyme Assays Using Substrates Labeled With Single Fluorophores", Anal Biochem, Feb. 26, 2015, vol. 477, pp. 69-77, Entire Document.
JP 2017-559035, Office Action dated Apr. 6, 2020, 14 pages.
EP 16793505.5, Extended Search Report dated Dec. 14, 2018, 6 pages.

* cited by examiner

*Primary Examiner* — Katherine D Salmon
(74) *Attorney, Agent, or Firm* — J. Clinton Wimbish; Nexsen Pruet, PLLC

(57) ABSTRACT

Described are methods of detecting modified nucleotide bases in a DNA sample using specific DNA glycosylases to excise target modified bases. DNA molecules are then labeled using a DNA polymerase lacking 3'→5' exo-nuclease activity and strand displacement activity. The methods can be used to detect epigenetic changes and DNA damage. Provided are methods for diagnosing a disease or condition, determining risk of a disease or condition, identifying appropriate treatment, monitoring effectiveness of treatment, and monitoring side effects of treatment in subjects based on detection of modified bases. Also provided are methods for determining environmental exposure, or an environmental exposure time, of a biological sample containing DNA. Also provided are kits, systems, and devices for performing the described methods.

13 Claims, 8 Drawing Sheets

IDENTIFICATION OF GENETIC MODIFICATIONS

CROSS-REFERENCE TO RELATED APPLICATIONS

This application is a U.S. national phase of International Application No. PCT/US2016/032029, filed on May 12, 2016, and published as International Publication No. WO 2016/183289 A1 on Nov. 17, 2016, which application claims the benefit of and priority to U.S. Provisional Patent Application No. 62/160,390 filed May 12, 2015, the contents of all of which are incorporated herein by reference in their entireties.

BACKGROUND

Methylation and the products of various forms of DNA damage have been implicated in a variety of important biological processes. Changes in methylation patterns and the appearance of damaged DNA are often among the earliest events observed for various disease states.

Epigenetic modifications are essential for normal development. For example, methylcytosine, the most widely studied epigenetic modification, is associated with a number of key processes including genomic imprinting, X-chromosome inactivation, suppression of repetitive elements, and carcinogenesis. For example, DNA methylation at the 5 position of cytosine has the specific effect of reducing gene expression and has been found in every vertebrate examined. In many disease processes, such as cancer, gene promoter CpG islands acquire abnormal hypermethylation, which results in transcriptional silencing that can be inherited by daughter cells following cell division. In addition, alterations of DNA methylation have been recognized as an important component of cancer development. Hypomethylation, in general, arises earlier and is linked to chromosomal instability and loss of imprinting, whereas hypermethylation is associated with promoters and can arise secondary to gene (oncogene suppressor) silencing. Additionally, hydroxymethylcytosine has also emerged as an important epigenetic modification as well with potential regulatory roles in gene expression ranging from development to aging. Various cancers have shown that hydroxymethylcytosine content is consistently and significantly reduced in malignant versus healthy tissues, even in early-stage lesions.

DNA is under constant stress from both endogenous and exogenous sources. The bases exhibit limited chemical stability and are vulnerable to chemical modifications through different types of damage, including oxidation, alkylation, radiation damage, and hydrolysis. Damage to DNA bases may affect their base-pairing properties and, therefore, may be mutagenic. DNA base modifications resulting from these types of DNA damage are wide-spread and play important roles in affecting physiological states and disease phenotypes. Examples include 7,8-dihydro-8-oxoguanine (8-oxoG) (oxidative damage), 8-oxoadenine (oxidative damage; aging, Alzheimer's, Parkinson's), 1-methyladenine, O6-methylguanine (alkylation; gliomas and colorectal carcinomas), benzo[a]pyrene diol epoxide (BPDE), pyrimidine dimers (adduct formation; smoking, industrial chemical exposure, UV light exposure; lung and skin cancer), and 5-hydroxycytosine, 5-hydroxyuracil, 5-hydroxymethyluracil, and thymine glycol (ionizing radiation damage; chronic inflammatory diseases, prostate, breast and colorectal cancer). For example, 8-oxoG is a frequent product of DNA oxidation. 8-oxoG tends to base-pair with adenine, giving rise to G•C to T•A transversion mutations. Another example is the hydrolytic deamination of cytosine and 5-methylcytosine (5-meC) to give rise to uracil and thymine mispaired with guanine, respectively, causing C•G to T•A transition mutations if not repaired. In another example, alkylation can generate a variety of DNA base lesions comprising 6-meG, N7-methylguanine (7-meG), or N3-methyladenine (3-meA). While 6-meG is promutagenic by its property to pair with thymine, 7-meG and 3-meA block replicative DNA polymerases and are therefore cytotoxic. These and many other forms of DNA base damage arise in cells many times times every day and only the continuous action of specialized DNA repair systems can prevent a rapid decay of genetic information. In addition to damage to nuclear DNA, mitochondrial DNA also experience significant oxidative damage, as well as damage from alkylation, hydrolysis, and adducts. For example, oxidative damage is the most prevalent type of damage in mitochondrial DNA, primarily because mitochondria are a major cellular source of reactive oxygen species (ROS). In addition, mitochondria house approximately 30% of the cellular pool of S-adenosylmethionine, which can methylate DNA nonenzymatically. Also, exposure to certain agents, such as estrogens, tobacco smoke, and certain chemicals, leads to preferential damage of mitochondrial DNA.

DNA repair is a collection of processes by which a cell identifies and corrects damage to the DNA molecules that encode its genome. Both normal metabolic activities and environmental factors can cause DNA damage. Many of these damaged sites cause structural damage to the DNA molecule and can alter or eliminate expression from an impacted gene sequence. Other lesions induce potentially harmful mutations in a cell's genome, which affect the survival of its daughter cells or can cause dysregulation that promotes development of disease state. As a consequence, the DNA repair process is constantly active as it responds to damage in the DNA structure.

As DNA damage and epigenetic modification may be the earliest indications of disease state, detection of epigenetic modification and DNA damage patterns can be useful for early detection of disease and intervention. However, detection methods have limitations. For example, with respect to methylation status, spectrophotometry can be used to indicate global content of a modification in target DNA, but has limited specificity. High-performance liquid chromatography (HPLC) and mass spectrometry are also often used, but are costly, require significant amounts of material, and reduce DNA to constituent nucleosides or nucleotides, thus destroying sequence information for downstream analysis. Immunoprecipitation (IP) using monoclonal antibodies can enrich DNA with target modifications, but limitations with specificity have been identified. Restriction digest profiling utilizes fragment analysis of DNA treated with modification-sensitive restriction endonucleases, but requires large amounts of material and is limited to sequences featuring a restriction site with known sensitivity. While bisulfite sequencing is considered the "gold-standard" technique for detection of DNA methylation, there are important limitations. First, the chemical conversion process causes widespread non-specific damage to DNA, and thus the approach requires large amounts of starting material. Second, the method can be expensive and time consuming, requiring multiple sequencing runs. Finally, and importantly, it is generally only applicable to methylcytosine (mC) modifications. Variations have been developed or suggested that allow a limited number of additional modification types to be targeted (methylcytosine (mC) and hydroxymethylcytosine (hmC)) but these are low-yield and still share the other limitations listed above. They are also not readily applicable to other modifications and are fairly complex.

BRIEF SUMMARY

Aspects of the present invention encompass detection of modified nucleotides, such as epigenetic changes and DNA damage, in DNA samples. Disclosed is a new, modular strategy for specific labeling of diverse epigenetic modifications and DNA damage with labeled nucleotides that can subsequently be used for enrichment, detection, and analysis of modified genetic sequences.

In one aspect, provided is a method of detecting a modified DNA base in a DNA sample, including (a) incubating a DNA sample comprising fragmented DNA with a DNA glycosylase that excises a modified nucleotide to form an apurinic or apyrimidinic site (AP site) at the site of the modified nucleotide in the fragmented DNA; (b) treating the fragmented DNA of step (a) with a DNA polymerase and a labeled nucleotide complimentary to a nucleotide opposite the AP site thereby incorporating the labeled nucleotide at the AP site in the fragmented DNA; (c) isolating the fragmented DNA containing the labeled nucleotide; and (d) detecting the position of the labeled nucleotide in the fragmented DNA to determine the location of the modified nucleotide in the DNA sample, quantitating the amount of labeled nucleotide in the fragmented DNA to determine amount of the modified nucleotide in the DNA sample, or both detecting the position and quantitating the amount of the labeled nucleotide in the fragmented DNA to determine the location and amount of the modified nucleotide in the DNA sample.

In one aspect, provided are methods useful for providing medical treatment to a subject. For example, the methods may be used to diagnose a subject with a disease known to be associated with an epigenetic modification or type of DNA damage. In another example, the methods may be used to identify a subject more or less likely to respond to a particular treatment for a disease. In another aspect, provided are methods for determining an appropriate treatment for a subject. In another example, the methods may be used to monitor the effect of a treatment on a subject to minimize side effects.

In another aspect, provided are methods of developing a genetic profile for a subject, including (a) providing a DNA sample from a subject; (b) fragmenting DNA in the DNA sample to produce fragmented DNA; (c) incubating a DNA sample comprising fragmented DNA with a plurality DNA glycosylases that excise a plurality of modified nucleotides, each DNA glycosylase excising a different kind of modified nucleotide, to form apurinic or apyrimidinic sites (AP sites) at the sites of the modified nucleotides in the fragmented DNA; (d) treating the fragmented DNA of step (c) with a DNA polymerase and labeled nucleotides complimentary to nucleotides opposite the AP sites, each kind of labeled nucleotide having a different kind of label, thereby incorporating the labeled nucleotides at the AP site in the fragmented DNA; (e) isolating the fragmented DNA containing the labeled nucleotides; and (d) detecting the positions of the labeled nucleotides in the fragmented DNA to determine the location of the modified nucleotides in the DNA sample, quantitating the amounts of labeled nucleotides in the fragmented DNA to determine amount of the modified nucleotides in the DNA sample, or both detecting the positions and quantitating the amounts of the labeled nucleotides in the fragmented DNA to determine the locations and amounts of the modified nucleotide in the DNA sample, thereby generating a genetic profile for the subject.

In another aspect, provided are methods of determining an environmental exposure time of a biological sample containing DNA, including (a) providing a DNA sample that has been exposed to an environmental condition; (b) fragmenting DNA in the DNA sample to produce fragmented DNA; (c) treating the fragmented DNA with a DNA polymerase and a labeled nucleotide complimentary to a nucleotide opposite the AP site thereby incorporating the labeled nucleotide at the AP site in the fragmented DNA; (c) isolating the fragmented DNA containing the labeled nucleotide; and (d) detecting the position of the labeled nucleotide in the fragmented DNA to determine the location of the modified nucleotide in the DNA sample, quantitating the amount of labeled nucleotide in the fragmented DNA to determine amount of the modified nucleotide in the DNA sample, or both; and (e) comparing the location, the amount, or both, of the modified nucleotide in the DNA sample to a plurality of reference samples that have been exposed to the environmental condition, each reference sample exposed to the environmental condition for a different length of time, wherein the environmental exposure time of the DNA sample is determined by the reference sample having the most similar location, amount, or both, of modified nucleotide as compared to the DNA sample.

Systems, devices, kits, and compositions are also described.

In one aspect, provided are kits for detection of a modified nucleotide in a DNA sample, including an enzyme selected from at least one of a DNA glycosylase, an AP endonuclease, a DNA polymerase lacking proofreading and strand displacement activity, or a DNA ligase; and at least one kind of labeled nucleotide.

In another aspect, provided is a plurality of oligonucleotides, each oligonucleotide comprising a known amount of a modified nucleotide.

In another aspect, provided is a sample device for detection of a modified nucleotide in a DNA sample, including a solid surface; a second solid surface in contact with the first solid surface; an inlet; and at least one chamber connected to the inlet and configured to perform at least one of (i) a base excision reaction, (ii) a DNA labeling reaction, (iii) isolation of labeled DNA, or (iv) at least one of DNA detection, quantitation, or sequencing.

In another aspect, provided is an analytical device, for detection of a modified nucleotide in a DNA sample, that includes a receptacle configured to receive one or more sample devices according to embodiment 44; a user input device; and a computing device comprising a memory and a processor, the memory comprising software instructions configured to cause the processor to execute one or more functions to perform at least one of (i) a base excision reaction, (ii) a DNA labeling reaction, (iii) isolation of labeled DNA, or (iv) at least one of DNA detection, quantitation, or sequencing.

The above described features, and many other features and attendant advantages of the present invention, will become apparent and further understood by reference to the following detailed description when considered in conjunction with the accompanying drawings.

present in a DNA molecule is excised with a specific DNA glycosylase and, optionally, an apurinic or apyrimidinic site (AP) endonuclease to generate a gap in a strand of the DNA molecule. The DNA molecule is then incubated with DNA polymerase and a labeled nucleotide complementary to the base in the DNA strand opposite the gap, resulting in incorporation of the label (B) at the original position of the modified base.

Figure 2:
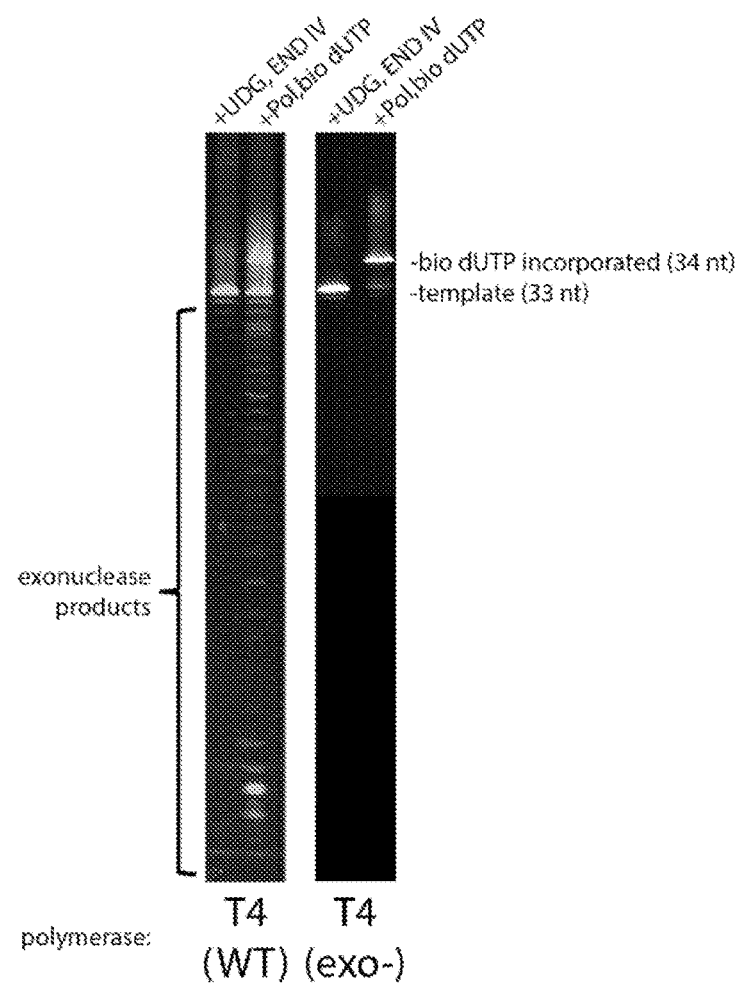

FIG. 2 depicts images of sequencing gel analysis of labeled DNA molecules into which biotinylated dUTP (bio dUTP) was incorporated using either wild type or mutant T4 DNA polymerase according to aspects of the disclosure. Uracil DNA glycosylase (UDG) was used to excise the uracil base from one strand of the 40 base pair dsDNA target, and then the target was treated with endonuclease IV (END IV), generating a single base pair gap between two fragments—a 5' 33 nucleotide fragment and a 6 nucleotide 3' fragment. The 33 nucleotide fragment is shown in the left side lane of each gel image. The dsDNA target was then treated with biotinylated dUTP (bio dUTP) and either wild type T4 DNA polymerase (WT T4 pol) or mutated T4 DNA polymerase lacking 3'→5' exonuclease activity (T4 pol exo−). The right side lane of each gel shows the resulting incorporation products.

Figure 3:
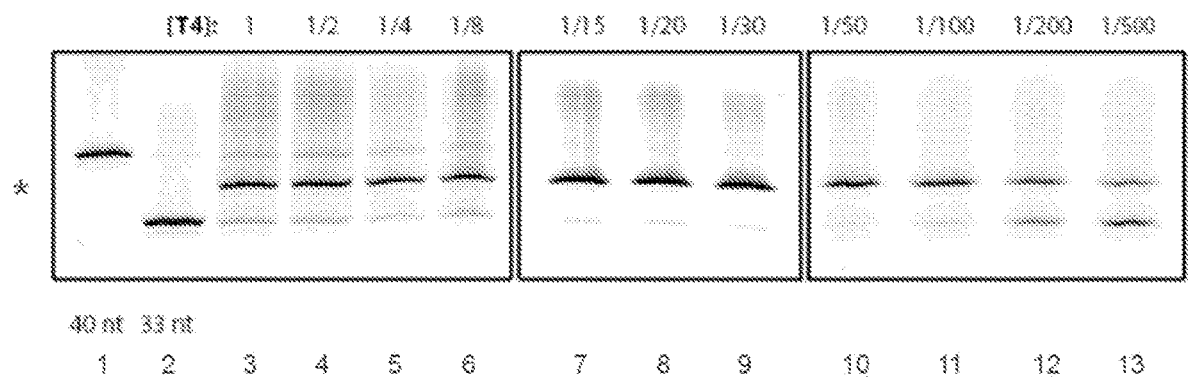

FIG. 3 depicts images of sequencing gel analysis of labeled DNA molecules into which biotinylated dUTP was incorporated using T4 pol exo− at various concentrations ranging from 1 Unit/nmol DNA to 1 Unit/pmol DNA. The assay format was generally as described above for FIG. 2. Lane 1 shows the migration position of the full length 40 nucleotide template strand, and lane 2 shows the migration position of the 33 nucleotide fragment generated by excision of the uracil. The asterisk shows the position of a 34 nucleotide fragment having one biotinylated dUTP incorporated into the 33 nucleotide strand. The dilution factor for the T4 pol exo− is shown for lanes 3-13 across the top of gel images.

Figure 4A:
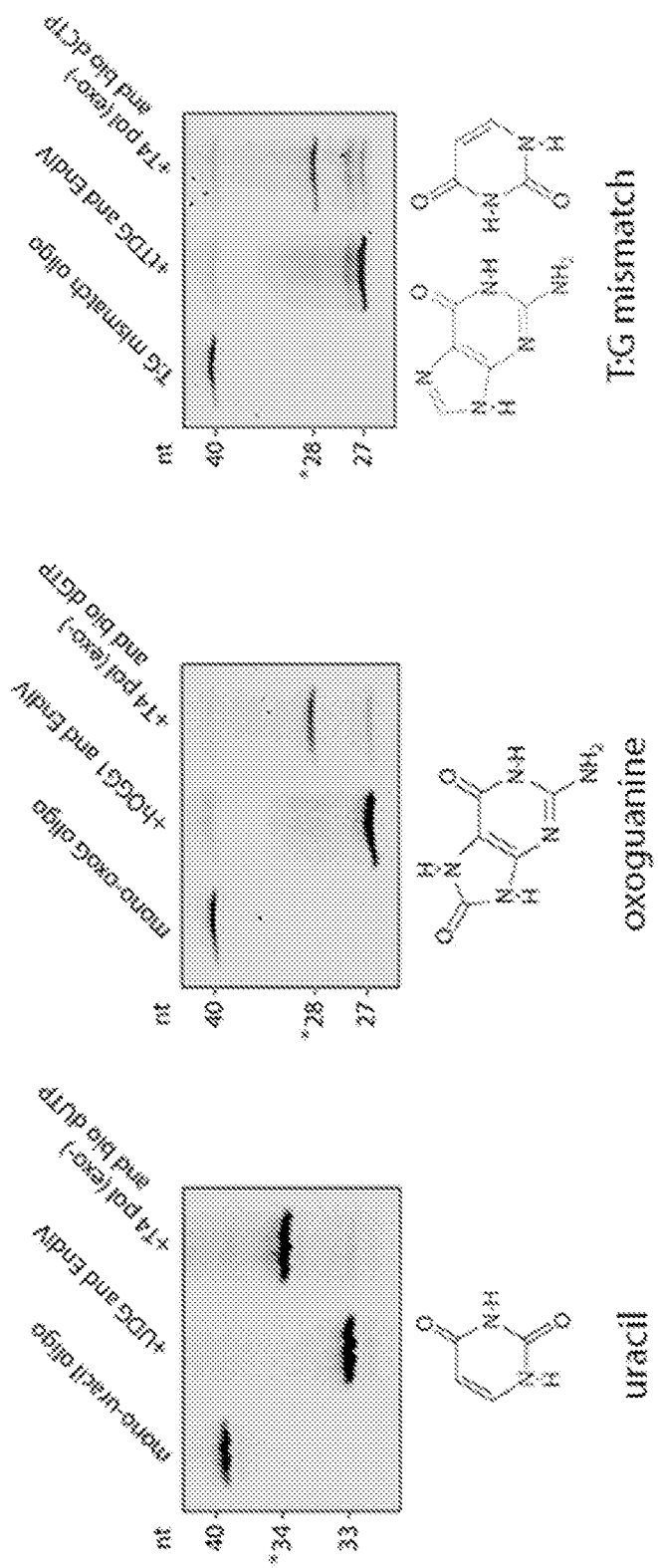

FIG. 4A depicts denaturing gels showing the specific cleavage and labeling of uracil, oxoguanine, and a T:G mismatch in DNA constructs using different DNA glycosylases according to aspects of this disclosure. The first lane in each gel is the intact 40 nt DNA molecule. The second lane shows the faster migrating cleavage product after excision of the target base by the glycosylase and endonuclease pair (uracil: UDG and Endo VI; oxoguanine: hOOG1 and Endo IV; T:G mismatch: TDG and Endo IV). The third lane shows the incorporation of a biotinylated base at the abasic site as the slower migrating DNA molecule (migration position marked with *).

Figure 4B:
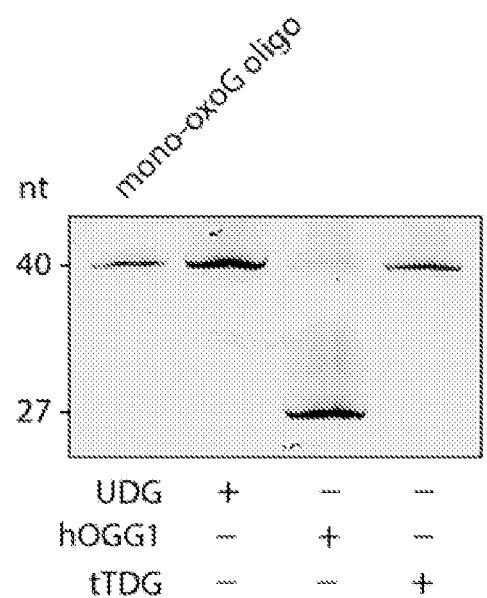

FIG. 4B depicts a denaturing gel illustrating the excision specificity of uracil DNA glycosylase (UDG), human oxoguanine glycosylase (hOGG1), and thymine DNA glycosylase (TDG) with respect to a 40 nt DNA construct having a single oxoG modification according to aspects of this disclosure. The strand from which the modification has been excised migrates at a faster rate.

Figure 4C:
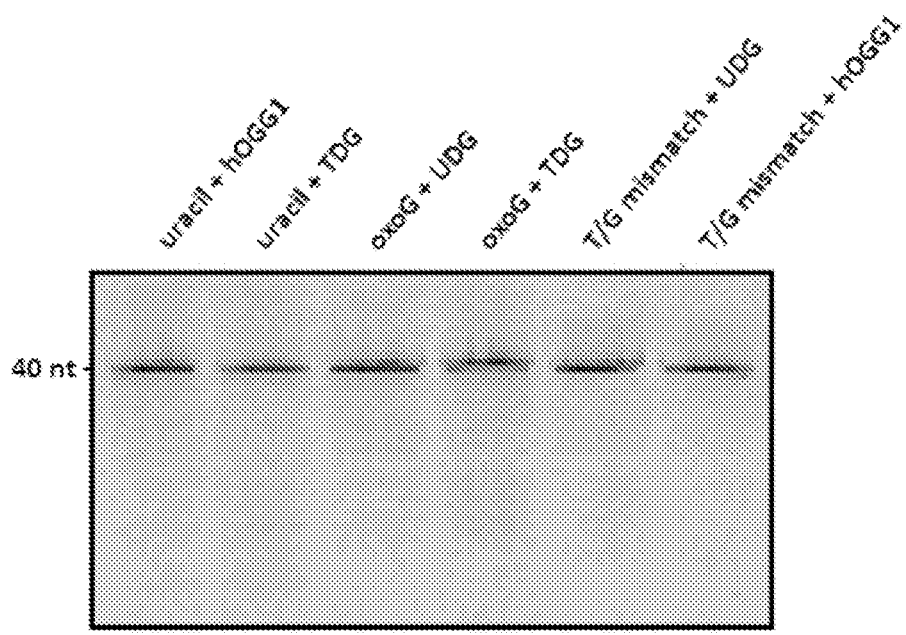

FIG. 4C depicts a denaturing gel showing the specificity of DNA glycosylases UDG, TDG, and hOGG1 according to aspects of this disclosure. The enzymes were each co-incubated with Endo IV and a 40 nt DNA molecule containing a single DNA modification different from the one that the DNA glycosylase is known to excise. Specifically, uracil-containing DNA construct was incubated with hOGG1 or TDG (specific for oxoG and T:G mismatches, respectively); an oxoG-containing DNA construct was incubated with UDG or TDG (specific for uracil and T:G mismatches, respectively); and a T:G mismatch-containing DNA construct was incubated with UDG or hOGG1 (specific for uracil and oxoG, respectively).

Figure 5:
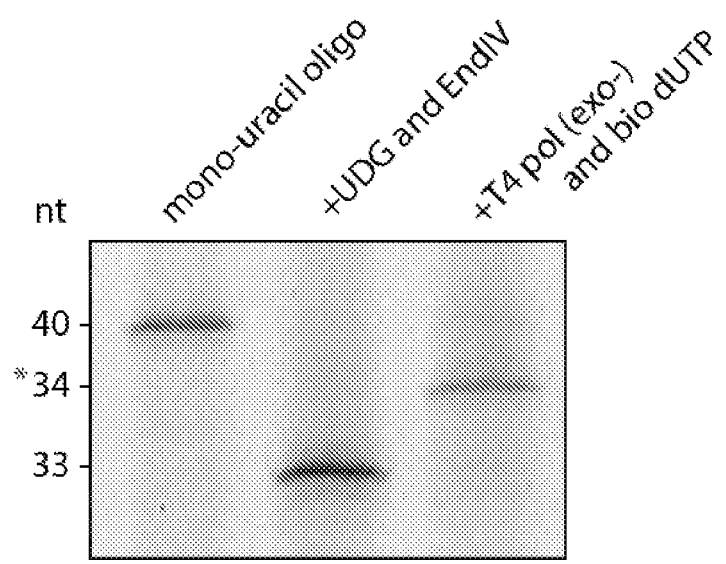

FIG. 5 depicts denaturing gel analysis of excision and labeling reactions performed in a tube (one pot reaction). The left lane shows the starting DNA construct containing a uracil. The middle lane shows the DNA product assessed in an aliquot taken from the reaction mixture after the excision step and prior to addition of the DNA polymerase to the reaction tube. The right lane shows the final labeled product produced after addition of and incubation with the DNA polymerase. The position of the labeled product is marked with a *.

Figure 6A:
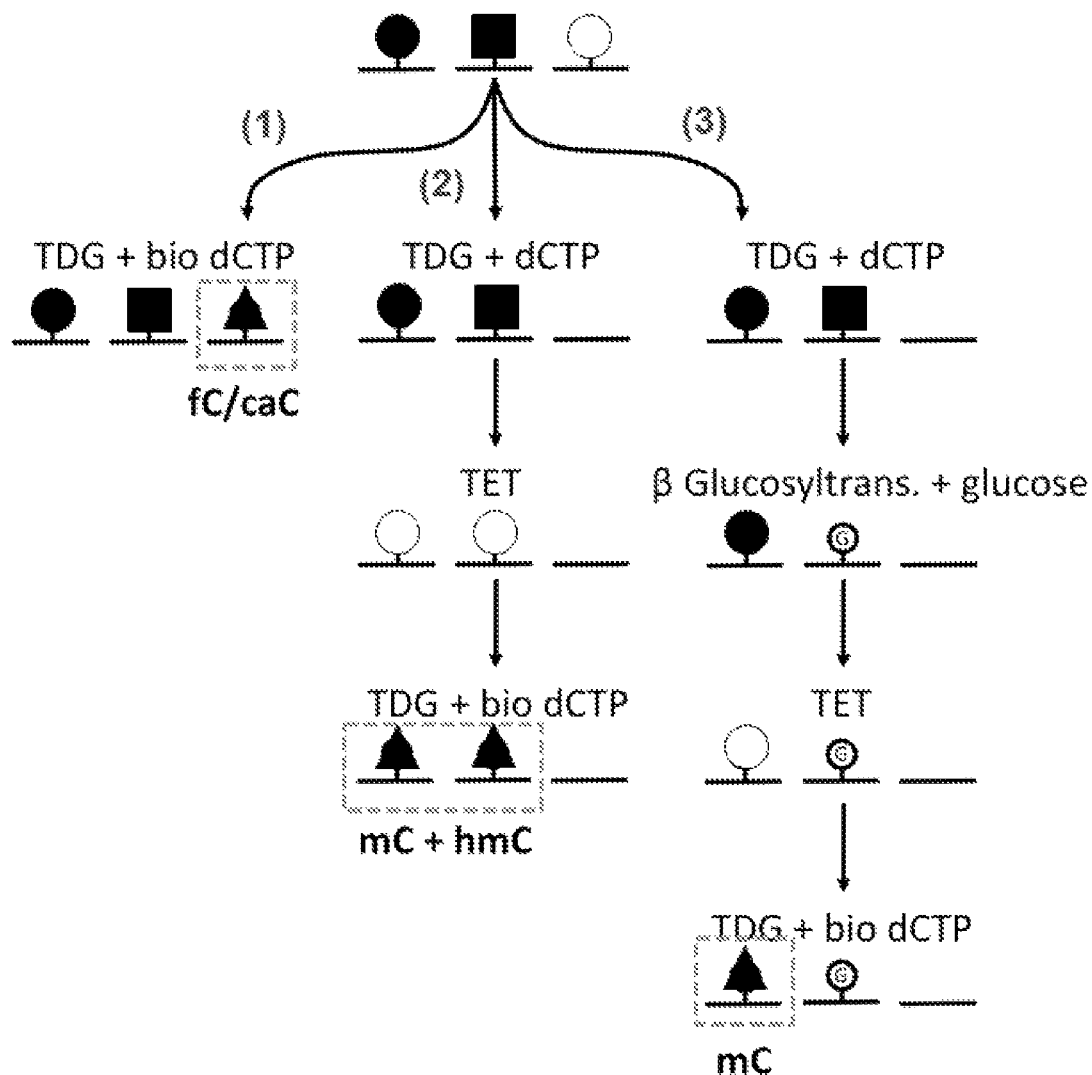

FIG. 6A depicts a schematic showing routes for detection of various modified DNA bases using thymine DNA glycosylase (TDG) according to aspects of this disclosure. In route (1), the DNA sample containing the modified bases is treated with TDG followed by labeling with biotinylated (bio) dCTP (triangle) to detect the positions of carboxycytosine (caC) and formylcytosine (fC) (white circle). In route (2), the DNA sample is treated with TDG followed by gap-filling using unlabeled nucleotides, then treated with TET enzyme to demethylate methylcytosine (mC, black circle) and hydroxymethylcytosine (hmC, square) to caC/fC (white circle), followed by TDG to excise the caC/fC, and then labeling with bio dCTP to detect the positions of mC and hmC. In route (3), the DNA sample is treated with TDG followed by gap-filling using unlabeled nucleotides, followed by treatment with β-glucosyltransferase to selectively attach a glucose moiety to hmC, followed by TET enzyme treatment to demethylate mC to caC/fC, followed by TDG to excise the caC/fC, and then labeling with bio dCTP to distinguish the positions of mC and hmC from each other.

Figure 6B:
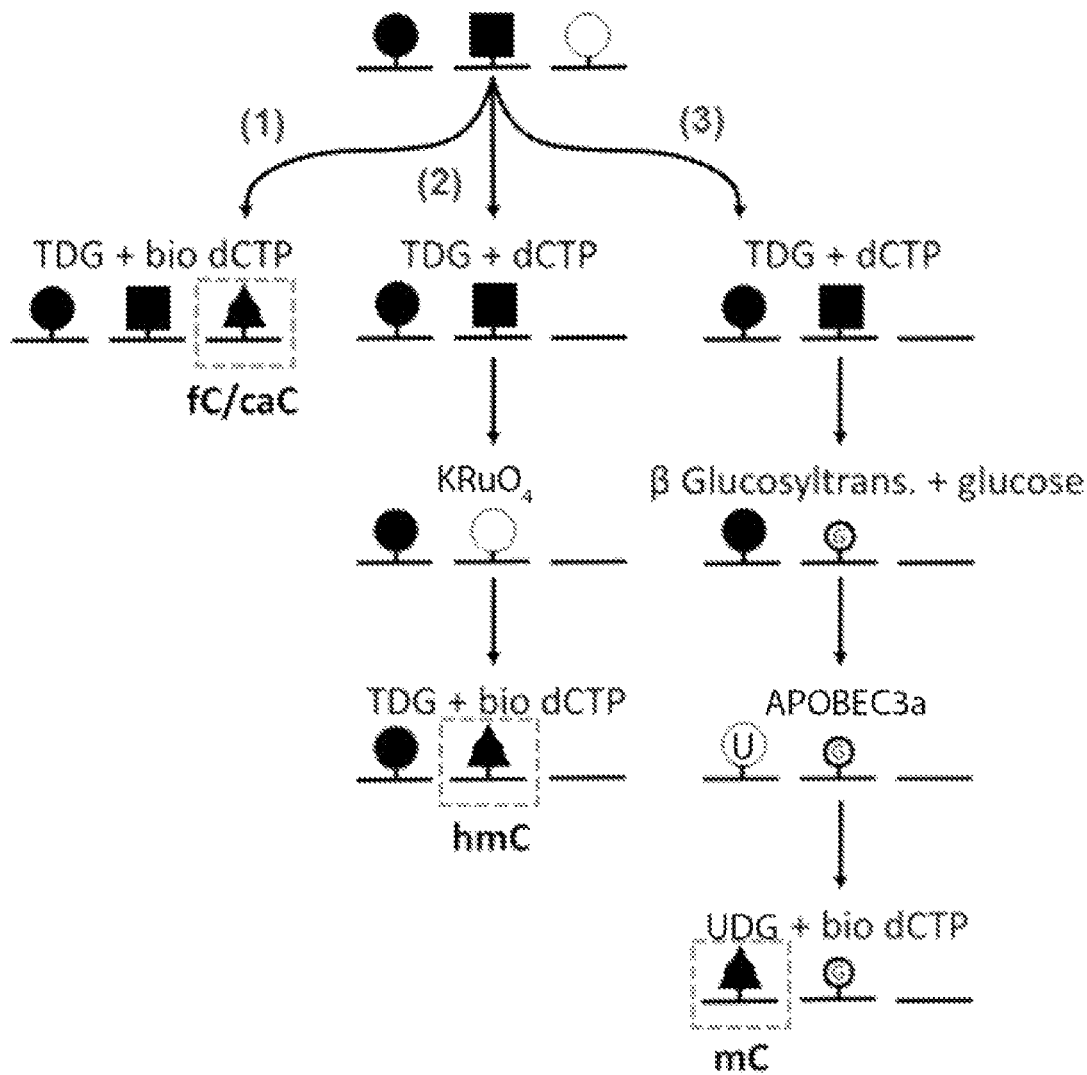

FIG. 6B depicts a schematic showing routes for detection of various modified DNA bases using thymine DNA glycosylase (TDG) and uracil DNA glycosylase (UDG) according to aspects of this disclosure. $KRuO_4$ can be used to oxidize hmC to caC/fC, which can then be cleaved by TDG, thereby labeling the site of hmC in the DNA sample with labeled dCTP (for example, biotinylated dCTP). A similar approach to that shown in FIG. 6A, treatment with β-glucosyltransferase can selectively attach a glucose moiety to hmC, thereby blocking it from oxidation. APOBEC3a (or, alternatively, bisulfite) can convert mC to uracil, which can then be cleaved by UDG and labeled with labeled dCTP (for example, biotinylated dCTP).

Figure 7:
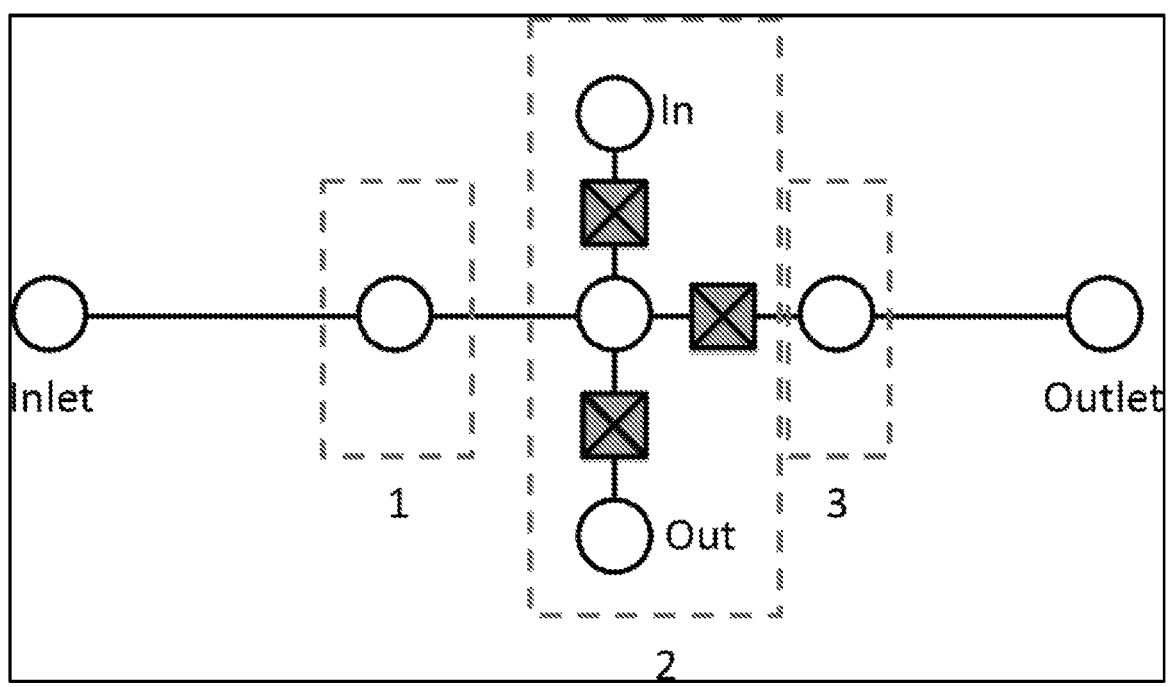

FIG. 7 depicts a sample device useful for performing the methods described herein according to aspects of the disclosure.

DETAILED DESCRIPTION

Described herein are methods of detecting modified nucleotides, such as epigenetic changes and DNA damage, in DNA samples.

I. Methods of Detecting Modified DNA Bases

In one aspect, provided are methods for detecting a modified DNA base in a DNA sample. An exemplary schematic overview of the methods is provided in FIG. 1. The methods may comprise obtaining a DNA sample and fragmenting the DNA. The methods may then involve treating the fragmented DNA with a DNA glycosylase that excises a modified nucleotide to form an apurinic or apyrimidinic site (AP site) in the fragmented DNA. The fragmented DNA may then be treated with a DNA polymerase and a labeled nucleotide corresponding to the excised modified nucleotide to incorporate the labeled nucleotide into the AP site. The fragmented DNA containing the labeled nucleotide may then be isolated, and the position of the labeled nucleotide in the fragmented DNA may be determined to identify the location of the modified nucleotide in the DNA sample. In some instances, the detecting step alternatively involves quantitating the amount of labeled nucleotides in the fragmented DNA, and the method further comprises comparing the amount of labeled nucleotides to the amount of labeled nucleotides in a reference sample containing a known amount of labeled nucleotides.

In one aspect, provided are methods useful for providing medical care to a subject. For example, the methods may be used to diagnose a subject with a disease or condition known to be associated with an epigenetic modification or type of DNA damage. As used herein, an epigenetic modification refers to covalent modification of DNA resulting in changes to its function and/or regulation, without altering the underlying genetic sequence. An epigenetic change is a heritable change in gene expression that does not involve changes to the underlying DNA sequence; a change in phenotype without a change in genotype. In another example, the methods may be used to determine whether a subject more or less likely to respond to a particular treatment for a disease or condition. In another example, the methods may be used to assess the effectiveness/efficacy of a treatment; that is responsiveness of a subject to treatment. In another example, the methods may be used to monitor the effect of a treatment on a subject to minimize side effects. In yet another example, the methods may include developing a genetic profile for a subject.

In one instance, provided are methods of diagnosing or detecting a disease or condition in a subject. The methods may comprise obtaining a DNA sample from the subject, fragmenting the DNA, treating the fragmented DNA with a DNA glycosylase that excises a modified nucleotide associated with the disease to form an apurinic or apyrimidinic site (AP site) in the fragmented DNA, treating the fragmented DNA with a DNA polymerase and a labeled nucleotide complimentary to a base opposite the AP site (for example, corresponding to the excised modified nucleotide to incorporate the labeled nucleotide into the AP site), isolating the fragmented DNA containing the labeled nucleotide, and detecting the position of the labeled nucleotide in the fragmented DNA to determine the location of the modified nucleotide in the DNA sample. In some instances, the detecting step alternatively involves quantitating the amount of labeled nucleotides in the fragmented DNA, and the method further comprises comparing the amount of labeled nucleotides to the amount of labeled nucleotides in a reference sample containing a known amount of labeled nucleotides. In some instances, epigenetic modifications may increase, decrease, or change pattern as compared to a healthy subject if the subject has the disease or condition. In certain cases, the subject may have increased amounts of DNA damage relative to a healthy subject if the subject has the disease or condition.

In another instance, provided are methods of identifying a subject at risk of developing a disease or condition. The methods may comprise obtaining a DNA sample from the subject, fragmenting the DNA, treating the fragmented DNA with a DNA glycosylase that excises a modified nucleotide associated with the disease to form an apurinic or apyrimidinic site (AP site) in the fragmented DNA, treating the fragmented DNA with a DNA polymerase and a labeled nucleotide corresponding to the excised modified nucleotide to incorporate the labeled nucleotide into the AP site, isolating the fragmented DNA containing the labeled nucleotide, and detecting the position of the labeled nucleotide in the fragmented DNA to determine the location of the modified nucleotide in the DNA sample. In some instances, the detecting step alternatively involves quantitating the amount of labeled nucleotides in the fragmented DNA, and the method further comprises comparing the amount of labeled nucleotides to the amount of labeled nucleotides in a reference sample containing a known amount of labeled nucleotides. In some instances, the DNA of the subject may be assessed for modified nucleotides associated with the disease more than once. For example, the subject may be monitored over time to determine if modified nucleotides accumulate in the DNA of the subject. In some instances, epigenetic modifications may increase, decrease, or change pattern as compared to a healthy subject if the subject is at risk of having the disease or condition. In certain cases, the subject may have increased amounts of DNA damage relative to a healthy subject if the subject has the disease or condition. In some instances, the subject has a hereditary risk of developing a disease or condition. In some cases, the subject has an environmental risk of developing a disease or condition.

In another instance, provided are methods of determining an appropriate treatment for a subject. The methods may comprise obtaining a DNA sample from the subject, fragmenting the DNA, treating the fragmented DNA with a DNA glycosylase that excises a modified nucleotide associated with responsiveness, or lack of responsiveness, to a treatment to form an apurinic or apyrimidinic site (AP site) in the fragmented DNA, treating the fragmented DNA with a DNA polymerase and a labeled nucleotide corresponding to the excised modified nucleotide to incorporate the labeled nucleotide into the AP site, isolating the fragmented DNA containing the labeled nucleotide, and detecting the position of the labeled nucleotide in the fragmented DNA to determine the location of the modified nucleotide in the DNA sample. In some instances, the detecting step alternatively involves quantitating the amount of labeled nucleotides in the fragmented DNA, and the method further comprises comparing the amount of labeled nucleotides to the amount of labeled nucleotides in a reference sample containing a known amount of labeled nucleotides. In some instances, multiple treatments are available for treatment of a disease or condition, subtype of a disease or condition. In some cases, the type, amount, and/or pattern of the DNA modifications detected in the DNA sample from the subject indicates that the subject has a disease or condition, or has a particular subtype of a disease or condition that is more likely to respond to a particular treatment.

In another instance, provided are methods for monitoring response of a subject to treatment. The methods may comprise obtaining a DNA sample from the subject, fragmenting the DNA, treating the fragmented DNA with a DNA glycosylase that excises a modified nucleotide associated with responsiveness (lack of disease state), or lack of responsiveness (disease state), to a treatment to form an apurinic or apyrimidinic site (AP site) in the fragmented DNA, treating the fragmented DNA with a DNA polymerase and a labeled nucleotide corresponding to the excised modified nucleotide to incorporate the labeled nucleotide into the AP site, isolating the fragmented DNA containing the labeled nucleotide, and detecting the position of the labeled nucleotide in the fragmented DNA to determine the location of the modified nucleotide in the DNA sample. In some instances, the detecting step alternatively involves quantitating the amount of labeled nucleotides in the fragmented DNA, and the method further comprises comparing the amount of labeled nucleotides to the amount of labeled nucleotides in a reference sample containing a known amount of labeled nucleotides. In some instances, the DNA of the subject may be assessed for modified nucleotides associated with the disease more than once. For example, the subject may be monitored over time to determine if the percent of modified nucleotides in the DNA of the subject, or the pattern of modified nucleotides therein, changes in response to treatment. For example, if the amount of modified nucleotides or the pattern thereof, or both, does not change over time as the subject receives the treatment, the subject may not be responding to treatment. Alternatively, if the amount of modified nucleotides or the pattern thereof, or both, does change over time as the subject receives the treatment, the subject may be responding to treatment. In one example, if the amount of DNA damage diminishes while the subject is receiving treatment, the subject may be responding to treatment.

In one instance, provided are methods of monitoring a subject for side effects associated with a treatment for a disease or condition. The methods may comprise obtaining a DNA sample from the subject, fragmenting the DNA, treating the fragmented DNA with a DNA glycosylase that excises a modified nucleotide associated with the treatment for the disease to form an apurinic or apyrimidinic site (AP site) in the fragmented DNA, treating the fragmented DNA with a DNA polymerase and a labeled nucleotide corresponding to the excised modified nucleotide to incorporate the labeled nucleotide into the AP site, isolating the fragmented DNA containing the labeled nucleotide, and detecting the position of the labeled nucleotide in the fragmented DNA to determine the location of the modified nucleotide in the DNA sample. In some instances, the detecting step alternatively involves quantitating the amount of labeled nucleotides in the fragmented DNA, and the method further comprises comparing the amount of labeled nucleotides to the amount of labeled nucleotides in a reference sample containing a known amount of labeled nucleotides. In some instances, the DNA of the subject may be assessed for modified nucleotides associated with the disease more than once. For example, the subject may be monitored over time to determine if modified nucleotides accumulate in the DNA of the subject. In some instances, the modified nucleotide associated with the treatment for the disease is DNA damage that accumulates in DNA of the subject as a result of the treatment. In some instances, the method further comprises indicating that amount of modified nucleotides is near or above a threshold, or has a pattern or profile, associated with negative side effects to the treatment and, in some instances, indicating that subject should not continue to receive the treatment and/or should receive an alternative treatment. In other instances, the method further comprises indicating that amount of modified nucleotides is below a threshold, or has a pattern or profile, not associated with negative side effects to the treatment and, in some instances, indicating that subject may continue to receive the treatment. In some instances, the treatment may be radiation therapy or chemotherapy.

For the above methods relating to determining an appropriate treatment for a subject, monitoring response of a subject to treatment, and monitoring a subject for side effects associated with a treatment for a disease or condition, various types of treatment are contemplated. In some instances, the treatment may be a pharmaceutical drug. Examples of pharmaceutical drugs include, but are not limited to cholinesterase inhibitors (ChEIs), N-methyl-D-aspartate (NMDA) receptor antagonists, carbidopa/levodopa and related compounds, dopamine agonists, anticholinergics, MAO-B inhibitors, COMT inhibitors, anti-inflammatory compounds (such as steroids, corticosteroids, non-steroidal anti-inflammatory drugs (NSAIDs)), immunosuppressive drugs, biologics (such as monoclonal antibodies, insulin, interferon, erythropoietin, G-CSF), analgesics, disease-modifying anti-rheumatic drugs (including biologic response modifiers), anticoagulants, antiplatelet compounds, angiotensin-converting enzyme (ACE) inhibitors, angiotensin II receptor inhibitors, beta blockers, combined alpha and beta blockers, calcium channel blockers, digitalis preparations, diuretics, vasodilators, vitamins, membrane-penetrating antioxidants, pyruvate, antiviral compounds, antibacterial compounds, and antifungal compounds, amongst others. In some instances, treatment may include altering any of the subject's diet, amount of physical activity, type of physical activity, or combination thereof.

In another instance, provided are methods of developing a genetic profile for a subject. The methods may comprise obtaining a DNA sample from the subject, fragmenting the DNA, treating the fragmented DNA with a plurality DNA glycosylases that excise modified nucleotides to form apurinic or apyrimidinic sites (AP sites) in the fragmented DNA, treating the fragmented DNA with a DNA polymerase and a labeled nucleotide corresponding to the excised modified nucleotides to incorporate the labeled nucleotide into the AP sites, isolating the fragmented DNA containing the labeled nucleotides, and detecting the position of the labeled nucleotides in the fragmented DNA to determine the location of the modified nucleotides in the DNA sample to determine the genetic profile for the subject. In some instances, the detecting step alternatively involves quantitating the amount of labeled nucleotides in the fragmented DNA, and the method further comprises comparing the amount of labeled nucleotides to the amount of labeled nucleotides in a reference sample containing a known amount of labeled nucleotides. In some instances, the fragmented DNA is treated with the plurality DNA glycosylases sequentially. In some instances, the fragmented DNA is aliquoted into separate containers and treated with the plurality DNA glycosylases in parallel. In some instances, the genetic profile for the subject may be compared to a DNA sample of unknown origin to determine if the DNA sample of unknown origin is from the subject. In some cases, more than one genetic profile for the subject may be developed over multiple points of time. The genetic profile for the subject may be compared from one time point to another to determine if the subject is developing a disease state or condition (such as described above with respect to the methods of providing medical care).

For the methods described above relating to providing medical care, the subject may have one or more of various diseases and conditions. In some instances, the disease or condition may be cancer. For example, the cancer may be a glioma, a colorectal cancer, a lung cancer, a skin cancer, a prostate cancer, or a breast cancer. In some instances, the disease or condition may be a neurodegenerative disease. For example, in some instances, the neurodegenerative disease may be Alzheimer's disease or Parkinson's disease. In some instances, the disease or condition may be a chronic inflammatory disease. For example, in some instances, the chronic inflammatory disease may be systemic lupus erythematosus (SLE) or rheumatoid arthritis (RA). In some instances, the disease or condition may be a metabolic disease. For example, the metabolic disease may be diabetes or obesity. In some instances, the disease or condition may be a cardiovascular disease. For example, the cardiovascular disease may be atherosclerosis or arteriosclerosis. In some instances, the disease or condition may be an infectious disease. For example, the infectious disease may be a bacterial infection, a viral infection, or a fungal infection. In some instances, the disease or condition may be a mitochondrial disease. For example, the mitochondrial disease may be mitochondrial myopathy; diabetes mellitus and deafness (DAD); Leber's hereditary optic neuropathy (LHON); Leigh syndrome; neuropathy, ataxia, retinitis pigmentosa, and ptosis (NARP), myonerogenic gastrointestinal encephalopathy (MNGIE); myoclonic epilepsy with ragged red fibers (MERRF); mitochondrial myopathy, encepalomyopathy, lactic acidosis, stroke-like symptoms (MELAS); or mitochondrial DNA depletion. In some instances, the disease or condition is one that arises from exposure to environmental (exogenous) agents. Examples of environmental agents include, but are not limited to, tobacco smoke, pollution, radiation (UV, X-ray, ionizing, nuclear, etc.), toxic chemicals or compounds such as, pesticides, toxic metals, chemical dispersants, industrial chemicals, oil and gas products and spills, chemotherapeutics, and biotoxins (fungal, microbial, plant, animal, short mycotoxins, short phytotoxins), as well as biological organisms, including bacteria, viruses, and fungi. In some instances, the disease or condition is one that arises from endogenous agents. Examples of endogenous agents include, but are not limited to, S-adenosylmethionine, which can methylate DNA nonenzymatically, and estrogen. Other diseases and conditions associated with epigenetic modification or DNA damage are also contemplated in relation to the methods provided herein.

In another instance, provided are methods of determining an environmental exposure time of a biological sample containing DNA. The reference sample is a biological sample that has been exposed to an environmental condition that causes modifications to DNA. The methods may comprise obtaining DNA from the biological sample, fragmenting the DNA, treating the fragmented DNA with a DNA glycosylase that excises a modified nucleotide to form an apurinic or apyrimidinic site (AP site) in the fragmented DNA, treating the fragmented DNA with a DNA polymerase and a labeled nucleotide corresponding to the excised modified nucleotide to incorporate the labeled nucleotide into the AP site, isolating the fragmented DNA containing the labeled nucleotide, and detecting the position of the labeled nucleotide in the fragmented DNA to determine the location of the modified nucleotides in the DNA sample to determine the DNA modification profile for the biological sample. In some instances, the detecting step alternatively involves quantitating the amount of labeled nucleotides in the fragmented DNA, and the method further comprises comparing the amount of labeled nucleotides to the amount of labeled nucleotides in a reference sample containing a known amount of labeled nucleotides. The amount of labeled nucleotides in the fragmented DNA may be compared to a plurality of reference samples that have been exposed to an environmental condition that causes modifications to DNA, each reference sample exposed for a different period of time, to determine the environmental exposure time of the DNA sample. Comparison of the DNA sample to the reference sample(s) may identify an environmental exposure time of the biological sample based on the amount of modified nucleotides in the DNA sample, the pattern thereof, or both, in comparison to that in the reference sample(s). In some instances, the environmental condition may include, but is not limited to, being outdoors. In some instances, the environmental condition is a specific outdoor environment (such as, for example, in water, buried in the ground, etc.). In some instances, the environmental condition may be exposure to oxidizing agent, alkylating agents, industrial chemicals, tobacco smoke, pollution, radiation (UV, X-ray, ionizing, nuclear, etc.), toxic chemicals or compounds such as, pesticides, toxic metals, chemical dispersants, oil and gas products and spills, chemotherapeutics, and biotoxins (fungal, microbial, plant, animal, short mycotoxins, short phytotoxins), as well as biological organisms, including bacteria, viruses, and fungi. In some instances, the biological sample may be obtained from a subject that is alive. In some instances, the biological sample may be obtained from a subject that is deceased.

In some instances, the DNA sample is genomic DNA, mitochondrial DNA, or both genomic and mitochondrial DNA, obtained from a biological sample.

For each the methods described above, in some instances, the modified nucleotide may be at least one of methylcytosine (mC), hydroxymethylcytosine (hmC), carboxycytosine (caC), formylcytosine (fC), 8-oxo-7,8-dihyroguanine (oxoG), uracil, methyladenine(mA), or 8-oxoadenine, O6-methylguanine, 1-methyladenine, O4-methylthymine, 5-hydroxycytosine, 5-hydroxyuracil, 5-hydroxymethyluracil, or thymine dimers. In some instances, a plurality of any combination of these types of modified nucleotides may be detected.

Also, in some instances, the DNA glycosylase may be one of the enzymes listed in Table 1. In some instances, the DNA polymerase does not have 3'→5' exonuclease activity or strand displacement activity. In one example, the DNA polymerase may be mutated T4 DNA polymerase lacking 3'→5' exonuclease activity. In some instances, the labeled nucleotide may be a biotin-labeled nucleotide. In some instances, the method further comprises incubating the fragmented DNA with an apurinic or apyrimidinic site (AP) endonuclease after treating the fragmented DNA with the DNA glycosylase. In some instances, the AP endonuclease may be Endonuclease IV. In some instances, the method further comprises incubating the fragmented DNA containing the labeled nucleotide with a DNA ligase to close nicks present in the fragmented DNA. Exemplary DNA ligases include T4 DNA ligase and *E. coli* DNA ligase. In some instances, isolating the fragmented DNA containing the labeled nucleotide may involve contacting the fragmented DNA with streptavidin attached to a solid support and removing fragmented DNA not bound thereto. In some instances, the detecting step may involve sequencing the isolated fragmented DNA.

Further details regarding the above-described methods are provided below.

Sample Preparation

In one aspect, DNA from a biological sample is obtained or provided. The DNA obtained or provided from the biological sample may be genomic DNA, mitochondrial DNA, or both genomic and mitochondrial DNA. In some instances, genomic DNA and mitochondrial DNA may be obtained separately from the same biological sample or source. Many different methods and technologies are available for the isolation of genomic DNA and mitochondrial DNA. In general, such methods involve disruption and lysis of the starting material followed by the removal of proteins and other contaminants and finally recovery of the DNA. Removal of proteins can be achieved, for example, by digestion with proteinase K, followed by salting-out, organic extraction, gradient separation, or binding of the DNA to a solid-phase support (either anion-exchange or silica technology). Mitochondrial DNA may be isolated similarly following initial isolation of mitochondria. DNA may be recovered by precipitation using ethanol or isopropanol.

There are also commercial kits available for the isolation of nuclear or mitochondrial DNA. The choice of a method depends on many factors including, for example, the amount of sample, the required quantity and molecular weight of the DNA, the purity required for downstream applications, and the time and expense.

In some instances, the isolated DNA is fragmented into a plurality of shorter double stranded DNA pieces. In general, fragmentation of DNA may be performed physically, or enzymatically.

For example, physical fragmentation may be performed by acoustic shearing, sonication, microwave irradiation, or hydrodynamic shear. Acoustic shearing and sonication are the main physical methods used to shear DNA. For example, the Covaris® instrument (Woburn, MA) is an acoustic device for breaking DNA into 100 bp-5 kb. Covaris also manufactures tubes (gTubes) which will process samples in the 6-20 kb for Mate-Pair libraries. Another example is the Bioruptor® (Denville, N.J.), a sonication device utilized for shearing chromatin, DNA and disrupting tissues. Small volumes of DNA can be sheared to 150 bp-1 kb in length. The Hydroshear® from Digilab (Marlborough, Mass.) is another example and utilizes hydrodynamic forces to shear DNA. Nebulizers, such as those manufactured by Life Technologies (Grand Island, N.Y.) can also be used to atomize liquid using compressed air, shearing DNA into 100 bp-3 kb fragments in seconds. As nebulization may result in loss of sample, in some instances, it may not be a desirable fragmentation method for limited quantities samples. Sonication and acoustic shearing may be better fragmentation methods for smaller sample volumes because the entire amount of DNA from a sample may be retained more efficiently. Other physical fragmentation devices and methods that are known or developed can also be used.

Various enzymatic methods may also be used to fragment DNA. For example, DNA may be treated with DNase I, or a combination of maltose binding protein (MBP)-T7 Endo I and a non-specific nuclease such as *Vibrio vulnificus* nuclease (Vvn). The combination of non-specific nuclease and T7 Endo synergistically work to produce non-specific nicks and counter nicks, generating fragments that disassociate 8 nucleotides or less from the nick site. In another example, DNA may be treated with NEBNext® dsDNA Fragmentase® (NEB, Ipswich, Mass.). NEBNext® dsDNA Fragmentase generates dsDNA breaks in a time-dependent manner to yield 50-1,000 bp DNA fragments depending on reaction time. NEBNext dsDNA Fragmentase contains two enzymes, one randomly generates nicks on dsDNA and the other recognizes the nicked site and cuts the opposite DNA strand across from the nick, producing dsDNA breaks. The resulting DNA fragments contain short overhangs, 5'-phosphates, and 3'-hydroxyl groups. Another example is the Nextera® Tagmentation® technology (Illumina, San Diego, Calif.). The Tagmentation® technology uses a transposase to simultaneously fragment and insert adapters onto dsDNA. Transoposomes have free DNA ends and insert randomly into DNA in a 'cut and paste' reaction. Because the DNA ends are free, this effectively fragments the DNA while adding on the adaptor sequences. This method may be useful where adaptor sequences may be useful for subsequent identification, isolation, or manipulation of samples.

In some instances, the DNA sample is fragmented into specific size ranges. For example, the DNA sample may be fragmented into fragments in the range of about 25-100 bp, about 25-150 bp, about 50-200 bp, about 25-200 bp, about 50-250 bp, about 25-250 bp, about 50-300 bp, about 25-300 bp, about 50-500 bp, about 25-500 bp, about 150-250 bp, about 100-500 bp, about 200-800 bp, about 500-1300 bp, about 750-2500 bp, about 1000-2800 bp, about 500-3000 bp, about 800-5000 bp, or any other size range within these ranges. For example, the DNA sample may be fragmented into fragments in the range of 25-100 bp, 25-150 bp, 50-200 bp, 25-200 bp, 50-250 bp, 25-250 bp, 50-300 bp, 25-300 bp, 50-500 bp, 25-500 bp, 150-250 bp, 100-500 bp, 200-800 bp, 500-1300 bp, 750-2500 bp, 1000-2800 bp, 500-3000 bp, 800-5000 bp, or any other size range within these ranges. For example, the DNA sample may be fragmented into fragments of about 50-250 bp. In one example, the DNA sample may be fragmented into fragments of 50-250 bp. In some instances, the fragments may be larger or smaller by about 25 bp. For example, the fragments may be larger or smaller by 25 bp. In some instances, relatively short DNA fragments may facilitate analysis by minimizing overlap of sequence between fragments.

In certain instances, the DNA fragments are treated to generate blunt end DNA fragments without nicks or gaps. This may be performed, for example, by incubating the fragmented DNA with a DNA polymerase and canonical nucleotides. A number of DNA polymerases will remove DNA overhangs and/or can be used to fill in missing bases if there is a 3' hydroxyl available for priming. Polymerases for such reactions include T4 DNA polymerase (no strand displacement activity), DNA polymerase I, the Klenow Fragment of DNA polymerase I (Klenow Fragment), Klenow exo minus polymerase, Taq DNA polymerase, Tfl DNA polymerase, Tth DNA polymerase, Tli DNA polymerase, and Pfu DNA polymerase. Each of these polymerases can be used to fill in 3' overhangs, while DNA polymerase I, Klenow Fragment, T4 DNA polymerase, Tli DNA polymerase, and Pfu DNA polymerase can also fill in 5' overhangs and remove 3' overhangs. In some instances, certain polymerases may be preferred to generate blunt ends, including, for example, T4 DNA polymerase (no strand displacement activity), Pfu DNA polymerase, Tli DNA polymerase, and the Klenow Fragment of DNA polymerase I. In some instances, certain polymerases may be preferred to fill internal gaps, including, for example, T4 DNA polymerase and human DNA polymerase β. In some instances, more than one DNA polymerase may be used to incorporate nucleotides into the DNA fragments. For example, in some instances, Taq DNA polymerase and T4 DNA polymerase may be used to generate blunt end DNA fragments without nicks or gaps.

In some instances, the DNA fragments may be further incubated with a ligase to enzymatically close nicks in the phosphate backbone of the DNA fragments. Ligase catalyzes the formation of a phosphodiester bond between juxtaposed 5' phosphate and 3' hydroxyl termini in duplex DNA or RNA. The enzyme will join blunt end and cohesive end termini as well as repair single stranded nicks in duplex DNA. An exemplary ligase is T4 ligase, which is the most frequently used enzyme for cloning. Another ligase that may be used is *E. coli* DNA ligase, which preferentially connects cohesive double-stranded DNA end but is also active on blunt ends DNA in the presence of Ficoll or polyethylene glycol. Another ligase that may be used is DNA ligase Ma, which is known to function in mitochondria.

In some instances, the DNA fragments may be modified to have a sample identifier sequence incorporated onto the 5' or 3' end. For example, this would allow analysis of multiple samples in one reaction in parallel and analysis of the final labeled DNA sample thereafter. For example, if the labeled DNA samples were analyzed by sequencing, the sequence identifier would allow next generation sequencing of multiple samples at the same time.

In some instances, DNA fragments may be modified to have a sequence incorporated onto, or moiety attached to, the 5' or 3' end to assist in isolation or analysis of the DNA fragments during the methods described herein. For example, a fluorescein amidite (FAM) label may be incorporated on either end of the DNA molecules, which can be used to assess the labeled DNA products by detecting fluorescence such as described, for example, in Examples 1 and 2. Another moiety that could be used is biotin, which can be used for detection or isolation through its strong interaction with streptavidin (which can be attached to a solid support to facilitate isolation of the DNA molecules). In another example, a sequence incorporated into each of the DNA molecules may be used to isolate them via hybridization to a complementary sequence affixed to a solid support. Other moieties useful for these purposes can be selected based on ease of attachment to DNA molecules and stability in the conditions used for performing the described method. In some instances, the sequence or moiety may be attached to the labeled DNA fragment after the labeling step of the method instead of before it.

Glycosylase Excision of Modified Nucleosides

In one aspect, the method includes incubating the DNA sample with a DNA glycosylase to excise modified bases. Many DNA glycosylases have been identified targeting a wide range of specific DNA damage elements, including sequence mismatches and a large range of epigenetic modifications. Exemplary genetic modifications detectable by the described methods include, but are not limited to, methylcytosine (mC), hydroxymethylcytosine (hmC), carboxycytosine (caC), formylcytosine (fC), 8-oxo-7,8-dihyroguanine (oxoG), uracil, methyladenine(mA), and others. The modular aspect of the described methods is that, through enzyme selection, many different specific modified nucleoside bases can be targeted independently.

There are two main classes of DNA glycosylases: monofunctional and bifunctional. Monofunctional glycosylases have only glycosylase activity, whereas bifunctional glycosylases also possess apurinic or apyrimidinic site (AP) lyase activity that permits them to cut the phosphodiester bond of DNA at a base lesion, creating a single-strand break without the need for an AP endonuclease. The AP-lyase activity cleaves 3' and 5' to the AP site leaving a 5' phosphate and a 3' phosphate. β-lyase activity (β-elimination of an AP site) yields a 3' α,β-unsaturated aldehyde adjacent to a 5' phosphate, which differs from the AP endonuclease cleavage product. Enzymes with β-lyase activity are referred to as Type/Class I AP endonucleases. Some glycosylase-lyases also have δ-lyase activity (can perform δ-elimination), which converts the 3' aldehyde to a 3' phosphate. Enzymes with β-lyase and δ-lyase activity are referred to as Type/Class II AP endonucleases. For example, *E. coli* Endonuclease III (Endo III) and Endonuclease VIII (Endo VIII) are bifunctional glycosylases that excise damaged pyrimidines from double-stranded DNA and have both N-glycosylase and an AP-lyase activity. Damaged bases recognized and removed by Endo III and VIII include urea, 5,6-dihydroxythymine, thymine glycol, 5-hydroxy-5-methylhydantoin, uracil glycol, 6-hydroxy-5,6-dihydrothymine, and methyltartronylurea. While Endo VIII and Endo III are similar, Endo VIII has β and δ lyase activity while Endo III has β lyase activity. Some enzymes are both DNA glycosylases and AP endonucleases; one example is Endo IV.

Exemplary DNA glycosylases that are useful in the described methods are listed in Table 1. In some instances, one or more of DNA glycosylases listed in Table 1 may be used in the described methods to excise modified bases from sample DNA. In some instances, a DNA glycosylase listed in Table 1 may be used to excise one or more of the modified bases listed in Table 1 as a substrate for the DNA glycosylase. While select DNA glycosylases are specifically identified in this disclosure, it is understood that any DNA glycosylase can be used in the performing the excision step of the described methods.

TABLE 1

DNA glycosylases.

| Type of Base Lesion/Modification | Name | Physiological Substrates | Fxn |
|---|---|---|---|
| Uracil in ss or ds DNA | Uracil-N glycoslyase 1 (UNG1/UDG1)* | U, 5-FU, ss and ds DNA | M |
| | Single-strand-specific monofnctional DNA glycoslyase I | U, 5-hmU, 5-FU, ss and ds DNA | M |
| Pyrimidine derivatives in mismatches | Methyl-binding domain glycosylase 4 (MBD4) | T, U, 5-FU, εC, opposite G, dsDNA | M |
| | Thymine DNA glycosylase (TDG) | T, U, 5-FU, εC, 5-hmU, 5-fC, 5-caC; opposite G, dsDNA | M |
| Oxidative base damage | 8-oxoG DNA glycosylase I (OGG1)* | 8-oxoG, FaPy, opposite C, dsDNA | B |
| | MutY homolog DNA glycosylase (MYH/MUTYH)* | A opposite 8-oxoG, C or G, 2-hA opposite G, ds DNA | M |
| Alkylated purines | Methylpurine glycosylase (MPG) | 3-meA, 7-meG, 3-meG, hypoxanthine, εA, ss and ds DNA | M |
| Oxidized, ring-fragmented or -saturated pyrimidines | Endonuclease III-like glycosylase 1 (NTHL1)* | Tg, FaPyG, 5-hC, 5-hU, dsDNA | B |
| | Endonuclease VIII-like glycosylase 1 (NEIL1)* | Tg, FaPyG, FaPyA, 8-oxoG, 5-hU, 5-hC, ss and ds DNA | B |
| | Endonuclease VIII-like glycosylase 2 (NEIL2)* | Same as NTHL1 and NEIL1 | B |
| | Endonuclease VIII-like glycosylase 3 (NEIL3) | FaPyG, FaPyA, prefers ssDNA | B |
| cis-syn-cyclobutane pyrimidine dimers (e.g., as caused by UV irradiation) | T4 pyrimidine dimer glycosylase (T4 PDG)/ T4 Endonuclease V | cis-syn-cyclobutane pyrimidine dimers | B |

TABLE 1-continued

DNA glycosylases.

| Type of Base Lesion/Modification | Name | Physiological Substrates | Fxn |
|---|---|---|---|
| Pyrimidine derivatives in mismatches | Mug-DNA glycosylase (MUG) | U, T, εC, opposite guanine | M |
| Damaged purines from dsDNA | FaPy-DNA glycosylase | 7,8-dihydro-8-oxoguanine (8-oxoguanine), 8-oxoadenine, fapy-guanine, methy-fapy-guanine, fapy-adenine, aflatoxin B1-fapy-guanine, 5-hydroxy-cytosine and 5-hydroxy-uracil | B |
| Alkylated purines | 3-methyladenine DNA glycosylase I (TagA) | 3-mA, 3-ethA | M |
| Alkylated purines | 3-methyladenine DNA glycosylase II (AlkA) | 3-m-purines, 7-m-purines, 3-eth-purines, 7-eth-purines, εA, $O^2$-m-pyrimidines | M |
| Uracil in ssDNA and dsDNA | SMUG DNA glycosylase (SMUG) | U, 5-hmU | M |
| Damaged pyrimidines | Endonuclease III | urea, 5,6-dihydroxythymine, thymine glycol, 5-hydroxy-5-methylhydantoin, uracil glycol, 6-hydroxy-5,6-dihydrothymine and methyltartronylurea | B |
| Damaged pyrimidines | Endonuclease VIII | urea, 5,6-dihydroxythymine, thymine glycol, 5-hydroxy-5-methylhydantoin, uracil glycol, 6-hydroxy-5,6-dihydrothymine, methyltartronylurea | B |

Legend:
U, uracil;
A, adenine;
T, thymine;
C, cytosine;
G, guanine;
ss, single stranded;
ds, double stranded;
5-h, 5-hydroxy;
5-hm, 5-hydroxymethyl;
5-FU, 5-fluoruracil;
ε, etheno;
5-fC, 5-formylcytosine;
5-caC, 5-carboxylcytosine;
8-oxoG, 8-oxo-7,8-dihyroguanine;
Tg, thymine glycol;
FaPy, 2,6-diamino-4-hydroxy-5-N-methylformamidopyrimindine;
m or me, methyl;
h, hydroxyl;
eth, ethyl;
Fxn, functionality;
M, monofunctional;
B, bifunctional;
*also found in mitochondria In some instances, once the AP site is generated by the DNA glycosylase, the DNA sample may then be treated with an AP endonuclease to generate a 3' hydroxyl group and a 5' deoxyribose 5'-phosphate flanking the position of the excised base. For example, where the DNA glycosylase used to excise the modified base is monofunctional, the phosphodiester backbone may be cleaved by treating the DNA sample with an AP endonuclease.

As discussed above, Type/Class I AP endonucleases (AP lyases) catalyze β-elimination at the 3' side of the AP site, while Type/Class II enzymes catalyze hydrolysis at the 5' side of the AP site, leaving a 3'-hydroxyl terminus. Type II enzymes include E. coli Endo III, Endo IV, and Endo VIII, Saccharomyces cerevisiae Apn 1, Drosophila melanogaster Rrp 1, Caenorhabditis elegans CeAPN1, and the major mammalian AP endonuclease, variously designated APE1 (also known as Ape, APEI, Hap1, Apex, REF1, and fibroblast AP endonuclease II). Several of the these Type II enzymes possess 3'→5' exonuclease activity, but all possess 3'-phosphodiesterase activity and have been shown to remove 3'-phosphoglycolates (PGs), phosphoglycoaldehydes, phosphates, and/or terminal AP sites from 3' end of DNA. In some instances, the AP endonuclease used in the described methods may also have 3' phosphodiesterase activity to excise the 3' phosphate remaining at the AP site.

In some instances, the excision step is performed using Endo IV, which can act on a variety of oxidative damage in DNA. Endo IV is an apurinic/apyrimidinic (AP) endonuclease that can hydrolyze intact AP sites in a dsDNA molecule. AP sites are cleaved at the first phosphodiester bond that is 5' to the lesion, leaving a hydroxyl group at the 3' terminus and a deoxyribose 5'-phosphate at the 5' terminus. The enzyme also has a 3'-diesterase activity and can release phosphoglycoaldehyde, intact deoxyribose 5-phosphate, and phosphate from the 3' end of DNA. In some instances, homologs of Endo IV may be used in the described methods, including, for example, Apn1, CeAPN1, or Rrp1. In some instances, the AP endonuclease is APE1. For example, APE1 may be used when analyzing nuclear or mitochondrial DNA.

In some instances, the DNA glycosylase may remain bound to a DNA molecule after excising a modified base or incorrect base. In such instances, the DNA molecule with the DNA glycosylase bound thereto may be incubated with a reagent to release the DNA glycosylase from the DNA molecule. Once the DNA glycosylase is released, the DNA molecule containing the abasic site may be labeled as described below and elsewhere in this disclosure. For example thymine DNA glycosylase (TDG) has poor catalytic efficiency (enzyme turnover). In some instances, when TDG is used as the DNA glycosylase in the described methods, the DNA product of the excision reaction (that is, a DNA molecule having an abasic site) may be further treated to remove the bound TDG. In one example, the DNA product may be incubated with proteinase K to degrade the TDG, thereby releasing it. In another example, the DNA-TDG mixture may be co-incubated with SUM01, which competitively binds to the DNA-binding domain of the glycosylase thereby resulting in its dissociation from the DNA molecule.

In some instances, the methods may be used to detect any of the modified bases listed in Table 1. In some instances, one or more of the following modified bases may be detected using the methods described herein: 5-fluoruracil (5-FU); 5-hydroxymethyl-fluoruracil (5-hmU); 5-formylcytosine (5-fC); 5-carboxylcytosine (5-caC); 8-oxo-7,8-dihyroguanine (8-oxoG); 2,6-diamino-4-hydroxy-5-N-methylformamidopyrimindine (FaPy); 2-hydroxy-adenine (2-hA); 7-methyl-guanine (7-meG); 3-methyl-guanine (3-meG); hypoxanthine; thymine glycol (Tg); uracil glycol (Ug); 5-hydroxy-cytosine (5-hC); 5-hydroxy-uracil (5-hU); cis-syn-cyclobutane pyrimidine dimers; 8-oxoadenine (8-oxoA); fapy-guanine (FaPyG); methy-fapy-guanine (mFaPyG); fapy-adenine (FaPyA); aflatoxin B1-fapy-guanine (AFB1-FaPyG); 5-hydroxy-cytosine (5-hC); 5-hydroxy-uracil (5-hU); 3-methyl-adenine (3-mA); 3-ethyl-adenine (3-ethA); 3-methyl-purines; 7-methyl-purines; 3-ethyl-purines; 7-ethyl-purines; etheno-adenine (εA); etheno-cytosine (εC); O2-methyl-pyrimidines; urea; 5,6-dihydroxythymine; 5-hydroxy-5-methylhydantoin; and 6-hydroxy-5,6-dihydrothymine; methyltartronylurea; methylcytosine (mC); and hydroxymethylcytosine (hmC). In one example, the methods described herein may be used to detect 8-oxo-7,8-dihyroguanine (8-oxoG). In some instances, the methods described herein may be used to detect one or more of 5-formylcytosine (5-fC); 5-carboxylcytosine (5-caC), methylcytosine (mC), and hydroxymethylcytosine (hmC).

In one example, the method may be used to detect any of a uracil nucleotide, an oxoguanine (oxoG) nucleotide, or a T:G mismatch in a DNA sample as shown, for example, in FIG. 4A. For example, the target DNA may be incubated with a combination of oxoG DNA glycosylase (hOGG1) and endonuclease IV (EndoIV) to excise oxoG and induce a nick suitable for polymerase activity. For example, the target DNA may be incubated with a combination of uracil DNA glycosylase and endonuclease IV (EndoIV) to excise uracil and induce a nick suitable for polymerase activity. For example, the target DNA may be incubated with thymidine DNA glycosylase to excise T:G mismatches, followed by incubation with proteinase K to degrade bound TDG, and finally endonuclease IV (EndoIV) to induce a nick suitable for polymerase activity. In each example, the DNA glycosylase will selectively target individual target nucleotides and excise them from the phosphate backbone of the DNA, leaving an apurinic or apyrimidinic (AP) site. Subsequently, for bifunctional glycosylases, the lyase activity of the enzyme will cleave 3' to the AP site, producing a 5' phosphate and a 3'-phospho-α,β-unsaturated aldehyde. Co-incubation with EndoIV will result in cleavage 5' to the AP site and hydroxylation of the 3' terminus, leaving a one nucleotide gap that acts as a substrate for polymerase activity. For monofunctional glycosylases, a remnant phosphate will remain 5' to the AP site. This does not affect subsequent polymerase activity. As discussed further in the next section of the disclosure, the DNA may be treated with biotin-labeled dNTP (where N matches the identity of the correct canonical base in the target) and T4 polymerase lacking 3'→5' exonuclease activity and strand displacement activity. The gap-filling capability of this polymerase results in only a single biotinylated nucleotide incorporated at each gap site, regardless of surrounding sequence. The resulting DNA fragments retain their original sequence but have a single biotin moiety at the location of each original target modified base or mismatch, respectively. In these examples, UDG and TDG are both monofunctional glycosylases while hOGG1 is bifunctional, thus demonstrating the applicability of the process to both classes of DNA glycosylases. In addition, the use of DNA glycosylases results in high specificity of target base excision and, thus, labeling. In some instances, a given DNA glycosylase will specifically excise its target base, while other DNA glycosylases will not. For example, as shown in FIG. 4B, UDG specifically excises oxoG from a target DNA molecule but hOGG1 and TDG do not. In another example, as shown in FIG. 4C, UDG does not excise oxoG or T:G mismatches, TDG does not excise oxoG or uracil, and hOGG1 does not excise uracil or T:G mismatches.

The DNA sample may be isolated, or purified, from the enzymes and other reagents used in the excision step of the method. Various methods can be used to isolate the DNA sample, including, but not limited to, column chromatography, phenol-chloroform treatment with ethanol precipitation, cesium chloride density gradients, anion exchange filtration, and silica adsorption. Following isolation, the DNA sample may be suspended in a buffer for storage or for use in the labeling step of the method described below.

Labeling of Target DNA at Excision Positions

In one aspect, the described methods involve the step of incubating the DNA fragments from which modified bases have been excised with a DNA polymerase and one or more labeled nucleotides so as to incorporate a labeled nucleoside base into the DNA sample at the positions where the modified bases initially were located. In some instances, the DNA polymerase has gap filling activity and does not have 3'→5' exonuclease or strand displacement activity. Exemplary DNA polymerases include, but are not limited to, mutated T4 DNA polymerase lacking 3'→5' exonuclease (proofreading) activity (T4 pol exo⁻ as sold, for example, by Lucigen), Tae Pol A, Sce Pol I, T2 pol, ASFV pol X, Human Pol lambda, Human Pol mu, Human Pol beta, Human Pol alpha, and Sce Pol alpha. In some instances, T4 pol exo⁻ may be used to incorporate labeled nucleotides into the gap created in the target DNA by excision of the targeted modified base. For example, in some instances, as shown in FIG. 2, labeling of target DNA with T4 pol exo⁻ results primarily in the desired reaction product in which labeled nucleosides were incorporated into the target DNA at the positions where modified bases were specifically excised. In some instances, use of a DNA polymerase that has gap filling activity and does not have 3'→5' exonuclease activity or strand displacement activity provides increased yield of the desired labeled product as compared to use of DNA polymerase having 3'→5' exonuclease activity, as shown in FIG. 2. Without being held to any particular theory, where the labeling reaction is performed using a DNA polymerase that has 3'→5' exonuclease activity, because the labeling reaction includes only one type of labeled nucleotide, degradation in the 3'→5' direction may cause the polymerase to either (i) pause permanently at a base 5' from the target, resulting in no label incorporation, or (ii) incorporate a labeled nucleoside at a site 5' from the targeted modified base, leaving a gap and misidentifying the position of the modified base. In some instances, the yield of the desired labeled product is at least about 50%, 55%, 60%, 65%, 70%, 75%, 80%, 85%, 90%, 95%, or nearly 100% of the total amount of target DNA in the labeling reaction. For example, the yield of the desired labeled product may be at least 50%, 55%, 60%, 65%, 70%, 75%, 80%, 85%, 90%, 95%, or nearly 100% of the total amount of target DNA in the labeling reaction. In one example, the yield of the desired labeled product may be at least 80%. In one example, the yield of the desired labeled product may be at least 85%. In another example, the yield of the desired labeled product may be at least 90%. In another example, the yield of the desired labeled product may be at least 95%. In another example, the yield of the desired labeled product may be at least 90% when the excision and labeling reactions are performed in a single reaction vessel without purification of the excision reaction intermediate product prior to the labeling reaction. In another example, the yield of the desired labeled product may be at least 95% when the excision and labeling reactions are performed in a single reaction vessel without purification of the excision reaction intermediate product prior to the labeling reaction. In some instances, use of a DNA polymerase lacking proofreading activity results in DNA molecules into which no labeled nucleosides are incorporated or excess labeled nucleotides are incorporated at spurious locations.

In some instances, the amount of DNA polymerase used in the labeling step of the method may be limiting thereby avoiding reduced yield of the desired product and generation of undesired products. In some instances, the amount of DNA polymerase used in the labeling reaction may be about 10 U/pmol to about 30 U/pmol total DNA in the labeling reaction. For example, the amount of DNA polymerase in the labeling reaction may be about 10 U/pmol total DNA, about 15 U/pmol total DNA, about 20 U/pmol total DNA, about 25 U/pmol total DNA, about 30 U/pmol total DNA, about 35 U/pmol total DNA, or an amount within 2-3 U/pmol of these amounts. In some instances, the amount of DNA polymerase in the labeling reaction may be 10 U/pmol total DNA, 15 U/pmol total DNA, 20 U/pmol total DNA, 25 U/pmol total DNA, 30 U/pmol total DNA, 35 U/pmol total DNA, or an amount within 2-3 U/pmol of these amounts. In one example, the amount of DNA polymerase is about 20 U/pmol total DNA in the labeling reaction. In some instances, the amount of DNA polymerase may be 20 U/pmol total DNA in the labeling reaction. In some instances, labeling reactions conducted using DNA polymerase concentrations of 50 U/pmol or greater may yield variable labeled products including products having one or more non-complementary labeled nucleoside into the target DNA, products in which no labeled nucleoside was incorporated, or both, as shown in FIG. 3. In some instances, labeling reactions conducted using less than 10 U/pmol DNA polymerase may result in reduced yield of the desired labeled product into which a single labeled nucleoside was incorporated at the position of the excised base. In some instances, the yield of the desired labeled product in the labeling step of the method is at least about 50%, 55%, 60 5, 65%, 70%, 75%, 80%, 85%, 90%, 95%, or nearly 100% of the total amount of target DNA treated. For example, the yield of the desired labeled product in the labeling reaction may be at least 50%, 55%, 60 5, 65%, 70%, 75%, 80%, 85%, 90%, 95%, or nearly 100% of the total amount of target DNA treated. For example, the yield of the desired labeled product may be at least 80%. In some instances, one Unit (U) is defined as the amount of the enzyme that produces a certain amount of enzymatic activity, that is, the amount that catalyzes the conversion of 1 micro mole of substrate per minute. For example, for T4 DNA polymerase, one Unit may incorporate 10 nmol of total deoxyribonucleotide into acid-precipitable material in 30 minutes at 37° C. using a DNase I-nicked DNA as template•primer under conditions such as 50 mM glycine-NaOH (pH 8.8), 16.6 mM $(NH_4)_2SO_4$, 6 mM $MgCl_2$, 6.5 µM EDTA, 10 mM 2-mercaptoethanol, 0.165 mg/ml BSA, 1.6 mg/ml DNase I-nicked salmon testes DNA, 0.33 mM dCTP, 0.33 mM dATP, 0.33 mM dGTP, 0.33 mM dTTP, 76 nM [$^3$H]dTTP, and enzyme in 0.1 ml for 30 min. at 37° C.

Various labels may be attached or conjugated to nucleotides for use in the labeling step of the method. In some instances, the label is selected based on a desired method of analysis for the labeled DNA product. In some instances, the label may be biotin. Thus, the labeling step of the method may be performed using biotinylated nucleotides. For example, as described in Examples 1-3, and shown in FIGS. 1-4, biotinylated dUTP may be used in a labeling reaction in which thymine (or modified forms thereof) have been excised from the DNA sample. Via its strong interaction with streptavidin, which can be attached to various solid supports, the biotin label can be used to specifically isolate labeled DNA molecules.

Other exemplary labels that could be used in the labeling step of the methods are digoxigenin and/or fluorescein, which are bound with high affinity and specificity by various anti-digoxigenin antibodies and anti-fluorescein antibodies, respectively, and can be used in a similar manner as described above for biotin and streptavidin.

Another exemplary label that could be used in the labeling step of the methods is based on the Azide-Alkyne Huisgen Cycloaddition reaction, which is one of the most popular reactions within the Click chemistry concept. This Click chemistry reaction uses a Copper (Cu) catalyst at room temperature to cause a 1,3-dipolar cycloaddition between an azide and a terminal or internal alkyne to give a 1,2,3-triazole. The Cu(I) species may either be introduced as preformed complexes, or are otherwise generated in the reaction pot itself by one of various ways. In some instances, nucleotides having an azide chemical group attached thereto may be used in the labeling step of the reaction. Following the labeling step, the Click chemistry may be performed to create a covalent bond to an alkyne-labeled analyte or substrate through cycloaddition for isolation and purification. In these cases, the substrate or analyte would be a solid support, such as a column or alkyne beads, to which the labeled DNA may be linked covalently and isolated. The linkage would subsequently be cleaved to release the labeled DNA.

Another exemplary label that could be used in the labeling step of the methods is an amine-reactive chemical group such as, for example, NHS esters (N-hydroxysuccinimide esters) and imidoesters. NHS esters are reactive groups formed by carbodiimide-activation of carboxylate molecule. NHS ester-activated crosslinkers and labeling compounds react with primary amines in physiologic to slightly alkaline conditions (pH 7.2 to 9) to yield stable amide bonds and release N-hydroxysuccinimide (NHS). Imidoester crosslinkers react with primary amines to form amidine bonds. Imidoester crosslinkers react rapidly with amines at alkaline pH but have short half-lives. In this way, a covalent bond could be formed selectively with an amine group on an analyte or substrate for subsequent isolation and purification. In these cases, the crosslinkers may be attached to a solid support, such as a column or alkyne beads, to which the labeled DNA may be linked covalently and isolated. The linkage may be subsequently cleaved to release the labeled DNA.

Another exemplary label that could be used in the labeling step of the methods is a Dithiol linker such as dithiol phosphoramidite (DTPA). DTPA can be inserted at any position in DNA molecule. After reduction with Tris(2-carboxyethyl)pophine (TCEP) or dithiothreitol (DTT), each insertion results in two thiol (SH) functional groups for coupling with ligands or surfaces. The dithiol modification may be used to couple the DNA fragments to ligands or solid surfaces, such as, for example, gold. It can also be used to link the DNA fragments to maleimides, halogens, iodacetamides, pyridyldisulfides, or to proteins, such as horseradish peroxidase or alkaline phosphatase. DPTA may then be used in a similar manner as described above for biotin/streptavidin, digoxigenin, and fluorescein.

In some instances, after the labeling is performed, the DNA fragments may be treated with a DNA ligase to seal any nicks in the phosphodiester backbone. This will result in a contiguous molecule that, in some instances, may be less prone to shear breakage and more amenable to amplification and other enzymatic processes used in analysis.

In some instances, DNA fragments from a given sample may be split into separate portions, with each portion being analyzed separately. In some instances, each portion may be analyzed using a different kind of DNA glycosylase. In some instances, at least some portions may be treated with one or more modifying enzymes and then treated with a DNA glycosylase as discussed further below.

In some instances, sequential addition of enzymes can be performed in a single reaction pot containing buffer suitable for activity of glycosylase, endonuclease, and polymerase. Performing each of the steps in a single reaction vessel may reduce loss of DNA material being analyzes by removing the need for DNA purification between each step. For example, as shown in FIG. 5, UDG, Endo IV, and T4 DNA pol exo⁻ may be used to specifically excise uracil from a DNA molecule and incorporate a labeled dUTP at the abasic site. In another example, hOGG1, Endo IV, and T4 DNA pol exo⁻ may be used to specifically excise oxoG from a DNA molecule and incorporate a labeled dGTP at the abasic site. In some instances, the efficiency of the excision and labeling reactions performed in a single reaction vessel, as described in Example 4, may be greater than the efficiency of performing the excision and labeling reactions separately. In another example, the yield of the desired labeled product may be at least 90% when the excision and labeling reactions are performed in a single reaction vessel without purification of the excision reaction intermediate product prior to the labeling reaction. In another example, the yield of the desired labeled product may be at least 95% when the excision and labeling reactions are performed in a single reaction vessel without purification of the excision reaction intermediate product prior to the labeling reaction.

Altering Glycosylase Targeting

In some instances, one DNA glycosylase may be used to facilitate excision and labeling of different kinds of modified bases. In some instances, the method may include additional steps in which the DNA fragments are treated with one or more enzymes that catalyze modifications to the bases of the DNA fragments that impacts their excision by a given DNA glycosylase. In some instances, modification of the DNA fragments with a modifying enzyme may alter a base such that it is no longer recognized and excised by a DNA glycosylase that typically would do so. In some instances, modification of the DNA with a modifying enzyme may alter a base such that it is recognized and excised by a DNA glycosylase that typically would not do so.

In one example, as described in Example 5 and shown in FIG. 6A, thymine DNA glycosylase (TDG) may be used to excise its known targets of carboxycytosine (caC) and formylcytosine (fC) and, with additional steps of modifying bases in a DNA sample, may be used to identify methylcytosine (mC) and hydroxymethylcytosine (hmC), which are modified bases that it does not specifically recognize. In one example, to label positions in the DNA having caC or fC modified bases, TDG may be used as the DNA glycosylase to generate an AP site at the position of these modified bases, and then labeled dTTP or dUTP can be incorporated to label these positions as shown for route (1) in FIG. 6A. In another example, to label and detect the position of mC and hmC modified bases, multiple steps using TDG and modifying enzyme TET may be used as shown in route (2) of FIG. 6A. For example, TDG may be used to excise any existing caC and fC modified bases present in the DNA, and the resulting AP sites may be filled with canonical (unlabeled) dTTP or dUTP. Then the DNA may be treated with TET enzyme to demethylate and convert mC and hmC modified bases into caC and fC. The DNA may then be treated with TDG again, which will generate AP sites at the position of the converted bases, and these sites may then be labeled with labeled dTTP or dUTP. In another example, to differentiate between mC and hmC, a portion of the DNA sample may be processed as described in route (2) and another portion may be processed in parallel to identify mC sites as shown in route (3) of FIG. 6A. The portion used to identify mC sites may treated with TDG to excise any existing caC and fC modified bases present in the DNA, and the resulting AP sites may be filled with canonical (unlabeled) dTTP or dUTP. The DNA may then be treated with β-glucosyltransferase to selectively attach a glucose moiety to hmC present in the DNA, followed by treatment with TET enzyme to convert only mC to caC/fC. The DNA may then be treated with TDG again to excise the converted caC/fC site (formerly mC sites), which may then be labeled with labeled dTTP or dUTP. Comparison of the portions of the DNA sample processed according to route (2) and route (3) will identify the hmC sites present in the DNA sample.

Other comparable methods for altering the selective excision of modified bases are possible. For example, a similar method may be performed to detect the same bases using thymine DNA glycosylase (TDG) and uracil DNA glycosylase (UDG), as shown in FIG. 6B. Route (1) to detect fC/caC is the same as described above. To specifically label and detect hmC in route (2), $KRuO_4$ can be used to oxidize hmC to caC/fC, which can then be cleaved by TDG, thereby labeling the site of hmC in the DNA sample with labeled dCTP (for example, biotinylated dCTP). In route (3), a similar approach to that shown in FIG. 6A may be used to detect mC specifically. β-glucosyltransferase can be used to selectively attach a glucose moiety to hmC, thereby blocking it from oxidation. Either APOBEC3a or bisulfite can convert mC to uracil, which can then be cleaved by UDG and labeled with labeled dCTP (for example, biotinylated dCTP).

In another example, the base excision step of the method may be performed in the presence of unlabeled competitor oligonucleotides containing one or more modified bases (all the same kind or more than one kind). For example, such oligonucleotides may be useful where a particular DNA glycosylase has the ability to excise more than one type of modified base (that is, has specificity for more than one type of modified base). The unlabeled competitor oligonucleotides may be combined with the fragmented DNA and the DNA glycosylase, and the unlabeled competitor oligonucleotides may contain a first type of modified base that is recognized by the DNA glycosylase. In some instances, the presence of the unlabeled competitor oligonucleotides may preferentially reduce the affinity of the DNA glycosylase for the first type of modified base and increase the affinity of the DNA glycosylase for a second type of modified base present in the fragmented genomic DNA.

In some instances, it may be desirable to treat the DNA sample with more than one DNA glycosylase in a sequential manner so as to differentially label different modified bases. For example, the method may include a first excision step with a first DNA glycosylase having specificity for a first modified base, and a first labeling step in which a first labeled nucleotide is incorporated into the DNA fragments. The method may also include a second excision step with a second DNA glycosylase having specificity for a second modified base, and a second labeling step in which a second labeled nucleotide is incorporated into the DNA fragments. The labels attached to the first and second labeled nucleotides may be different labels. The method may include additional excision steps with DNA glycosylases having different specificities, and labeling steps with labeled nucleotides having different labels from the first and second labeled nucleotides. In some instances, sequential rounds of excision and labeling may permit detection of multiple types of modified bases in a single DNA sample. In some instances, the DNA sample may be split into a plurality of portions and the excision step performed on each in parallel with different DNA glycosylases. In some instances, the same label may be used on the labeled nucleotides for each separate portion where the labeled DNA molecules in each portion of the sample will be detected and analyzed separately. In some instances, it may be desirable to use different labels for each portion so that the portions can be combined and analyzed at the same time.

Enrichment of Labeled DNA

In some instances, labeled DNA fragments may be isolated or enriched from the total DNA sample prior to label detection. As described above, the label that is incorporated into the DNA fragments may be used. For example, streptavidin can be used to isolate DNA labeled with biotin, antibodies can be used to isolate DNA labeled with digoxigenin or fluorescein, and gold, for example, can be used to isolate DNA labeled with DTPA. Azide modified molecules can be isolated using alkyne-agarose resin columns, and amine chemistry can be used to enrich such molecules with glass beads.

The enrichment step will be described with respect to biotin labeled DNA for simplicity. However, analogous methods are readily apparent based on the type of label used in the labeling step of the method. In one example, the DNA fragments may be labeled with biotinylated nucleosides. Following the labeling step of the method, the DNA fragments may be incubated with streptavidin magnetic beads so that the fragments containing labeled bases (in place of where modified bases were present in the starting DNA sample) are affinity captured. A magnetic field may then be used to pull down the beads while the unlabeled DNA fragments in solution are washed away. The labeled DNA fragments may then be cleaved from the streptavidin beads using treatment with 95% formamide and 10 mM EDTA (pH 8.2) at elevated temperature and isolated by decanting the supernatant under magnetic field.

In some instances, the label is removed from the enriched DNA fragments. For example, the label may be removably attached to the nucleotide used for labeling such that, after incorporation into the target DNA, it is removably attached to the base incorporated into the labeled target DNA. In one example, the label may be attached to the nucleotide (base) via a photocleavable linker. The base may then be removed by light exposure (such as provided by a laser) to release the label. In another example, the label may be attached via a chemically cleavable linker. For example, the chemically cleavable linker may be a moiety cleavable by acid, base, oxidation, reduction, heat, light, metal ion catalysis, displacement, or elimination chemistry.

Analysis of Labeled DNA

In some instances, once target modifications are labeled as described above, they can be assessed through a number of established and emerging techniques, including, but not limited to, deep sequencing, next generation sequencing, and nanopore technology as described in U.S. Patent Application Nos. 2013/0196323, 2013/0203050, and 2014/0319339, which are incorporated herein by reference in their entireties. For example, the analysis method may be based on the label selected for identification. Some methods are more quantitative than others. In one example, sequencing analysis may be used to analyze the labeled DNA molecules. The isolated labeled DNA may be amplified using random hexamers, sequenced, and the sequence compared to a reference library such that all captured sequences can be identified and assigned a relative abundance. In another example, nanopores may be used to analyze the labeled DNA molecules. Labeled DNA sequences of a short length (≥500 bp) may be selectively translocated through a nanometer-scale aperture, resulting in signature variations in measured trans-pore ionic current that can be used to quantify the labeled DNA directly without amplification.

In some instances, control DNA oligonucleotides containing one or more modified bases (of the same kind or of different kinds) may be used to quantitate the amount of the modified bases in the isolated labeled DNA. The control DNA oligonucleotides may be of a known concentration and have a known amount of modified base per DNA molecule or concentration. In some instances, the control DNA oligonucleotide may be of a similar size to the isolated label DNA fragments. In some instances, the described base excision and labeling reactions may be performed on the isolated labeled DNA and the control DNA oligonucleotides in parallel. Analysis of the amount of labeling of the control DNA oligonucleotides may be used to quantitate the amount of label incorporated into the isolated labeled DNA and, thus, the amount of a particular modified base in the isolated labeled DNA. In one example, a standard curve may be generated based on labeling incorporated into a plurality of amounts of a control DNA oligonucleotide, and the amount of labeling incorporated into the isolated labeled DNA may be compared to the standard curve to determine the amount of the modified base present in the isolated labeled DNA. In some instances, the analysis may be performed comparing a plurality of control DNA oligonucleotides to the isolated labeled DNA, each control DNA oligonucleotide having a known amount of a different modified base. In another example, the control DNA oligonucleotides may be combined with the isolated labeled DNA at a known amount (spiked in) for quantitation.

Non-limiting embodiments include:

Embodiment 1. A method of detecting a modified DNA base in a DNA sample, comprising:

(a) incubating a DNA sample comprising fragmented DNA with a DNA glycosylase that excises a modified nucleotide to form an apurinic or apyrimidinic site (AP site) at the site of the modified nucleotide in the fragmented DNA;

(b) treating the fragmented DNA of step (a) with a DNA polymerase and a labeled nucleotide complimentary to a nucleotide opposite the AP site thereby incorporating the labeled nucleotide at the AP site in the fragmented DNA;

(c) isolating the fragmented DNA containing the labeled nucleotide; and (d) detecting the position of the labeled nucleotide in the fragmented DNA to determine the location of the modified nucleotide in the DNA sample, quantitating the amount of labeled nucleotide in the fragmented DNA to determine amount of the modified nucleotide in the DNA sample, or both detecting the position and quantitating the amount of the labeled nucleotide in the fragmented DNA to determine the location and amount of the modified nucleotide in the DNA sample.

Embodiment 2. The method of embodiment 1, wherein the DNA sample is genomic DNA, mitochondrial DNA, or a combination thereof.

Embodiment 3. The method of embodiment 1 or 2, wherein the DNA sample comprises DNA fragments about 50-250 base pairs in length.

Embodiment 4. The method of any of embodiments 1 to 3, where in the modified nucleotide is at least one of methylcytosine (mC), hydroxymethylcytosine (hmC), carboxycytosine (caC), formylcytosine (fC), 8-oxo-7,8-dihyroguanine (8-oxoG), uracil, methyladenine(mA), 8-oxoadenine, O6-methylguanine, 1-methyladenine, O4-methylthymine, 5-hydroxycytosine, 5-hydroxyuracil, 5-hydroxymethyluracil, or thymine dimers.

Embodiment 5. The method of any preceding claim, where in the modified nucleotide is at least one of those listed in Table 1.

Embodiment 6. The method of any of embodiments 1 to 5, wherein the DNA glycosylase is at least one of those listed in Table 1.

Embodiment 7. The method of any of embodiments 1 to 6, further comprising incubating the fragmented DNA of step (a) with an AP endonuclease before performing step (b).

Embodiment 8. The method of any of embodiments 1 to 7, wherein the DNA polymerase does not have 3'→5' exonuclease activity or strand displacement activity.

Embodiment 9. The method of any of embodiments 1 to 8, wherein the DNA polymerase may be mutated T4 DNA polymerase lacking 3'→5' exonuclease activity.

Embodiment 10. The method of any of embodiments 1 to 9, wherein the amount of DNA polymerase used in step (b) may be about 10 U/pmol to about 30 U/pmol total DNA.

Embodiment 11. The method of any of embodiments 1 to 10, wherein the labeled nucleotide is biotin-labeled nucleotide.

Embodiment 12. The method of any of embodiments 1 to 11, wherein isolating the fragmented DNA containing the labeled nucleotide comprises contacting the fragmented DNA with streptavidin attached to a solid support and removing fragmented DNA not bound thereto when the labeled nucleotide is biotin-labeled nucleotide.

Embodiment 13. The method of any of embodiments 1 to 12, wherein quantitating the amount of labeled nucleotides in the fragmented DNA, and the method further comprises comparing the amount of labeled nucleotides to the amount of labeled nucleotides in a reference sample containing a known amount of labeled nucleotides.

Embodiment 14. The method of any of embodiments 1 to 13, wherein detecting the position of the labeled nucleotide comprises sequencing the isolated fragmented DNA.

Embodiment 15. A method of diagnosing a subject with a disease or condition known to be associated with an epigenetic modification or type of DNA damage, comprising:

(a) providing a DNA sample from the subject;

(b) fragmenting DNA in the DNA sample to produce fragmented DNA;

(c) detecting a modified DNA base in the DNA sample according to the method of claim 1 thereby identifying at least one of the location or amount of the modified nucleotide in the DNA sample;

(d) determining differences in the location or the amount of the modified nucleotide in the DNA sample in comparison to the location or amount of the modified base in one or more reference samples from one or more healthy subjects; and (e) indicating that the subject has the disease or condition if there are differences in the location or the amount of the modified nucleotide in the DNA sample as compared to the location or amount of the modified base in one or more reference samples from one or more healthy subjects.

Embodiment 16. The method of embodiment 15, comprising indicating that the subject has the disease or condition if there is an increased amount of the modified nucleotide in the DNA sample as compared to the amount of the modified base in the one or more reference samples from one or more healthy subjects.

Embodiment 17. The method of embodiment 15, comprising indicating that the subject has the disease or condition if there is a decreased amount of the modified nucleotide in the DNA sample as compared to the amount of the modified base in the one or more reference samples from one or more healthy subjects.

Embodiment 18. The method of embodiment 15, comprising indicating that the subject has the disease or condition if there is there is a change in the location of the modified nucleotide in the DNA sample as compared to the location of the modified base in the one or more reference samples from one or more healthy subjects.

Embodiment 19. A method of identifying a subject at risk of developing a disease or condition known to be associated with an epigenetic modification or type of DNA damage, comprising:

(a) providing a DNA sample from the subject;

(b) fragmenting DNA in the DNA sample to produce fragmented DNA;

(c) detecting a modified DNA base in the DNA sample according to the method of claim 1 thereby identifying at least one of the location or amount of the modified nucleotide in the DNA sample;

(d) determining differences in at least one of the location or the amount of the modified nucleotide in the DNA sample in comparison to the location or amount of the modified base in one or more reference samples from one or more healthy subjects; and (e) indicating that the subject is at risk of developing the disease or condition if there are differences in at least one of the location or the amount of the modified nucleotide in the DNA sample as compared to the location, the amount, or both, of the modified base in one or more reference samples from one or more healthy subjects.

Embodiment 20. The method of embodiment 19, comprising indicating that the subject is at risk of developing the disease or condition if there is an increased amount of the modified nucleotide in the DNA sample as compared to the amount of the modified base in the one or more reference samples from one or more healthy subjects.

Embodiment 21. The method of embodiment 19, comprising indicating that the subject is at risk of developing the disease or condition if there is a decreased amount of the modified nucleotide in the DNA sample as compared to the amount of the modified base in the one or more reference samples from one or more healthy subjects.

Embodiment 22. The method of embodiment 19, comprising indicating that the subject is at risk of developing the disease or condition if there is there is a change in the location of the modified nucleotide in the DNA sample as compared to the location of the modified base in the one or more reference samples from one or more healthy subjects.

Embodiment 23. The method of any one of embodiments 19 to 22, wherein the subject has a hereditary risk of developing the disease or condition.

Embodiment 24. The method of any one of embodiments 19 to 22, wherein the subject has an environmental risk of developing the disease or condition.

Embodiment 25. The method of any one of embodiments 19 to 24, wherein the method is performed at a future point in time to monitor the subject if there are not differences in the location or the amount of the modified nucleotide in the DNA sample as compared to the location or amount of the modified base in one or more reference samples from one or more healthy subjects.

Embodiment 26. A method of determining the likeliness of a subject to respond to a treatment for a disease or condition, comprising:
 (a) providing a DNA sample from the subject;
 (b) fragmenting DNA in the DNA sample to produce fragmented DNA;
 (c) detecting a modified DNA base in the DNA sample according to the method of claim 1 thereby identifying at least one of the location or the amount of the modified nucleotide in the DNA sample;
 (d) determining differences in the location or the amount of the modified nucleotide in the DNA sample in comparison to at least one of the location or amount of the modified base in samples from a reference population of subjects having the disease or condition and known to be responsive to the treatment; and
 (e) indicating that the subject more likely to respond to the treatment if at least one of the location or the amount of the modified nucleotide in the DNA sample is similar to the location, the amount, or both, of the modified base in the samples from the reference population, or indicating that the subject less likely to respond to the treatment if at least one of the location or the amount of the modified nucleotide in the DNA sample is not similar to the location, the amount, or both, of the modified base in the samples from the reference population.

Embodiment 27. A method of assessing responsiveness of a subject to a treatment, comprising:
 (a) providing a DNA sample from a subject who is receiving the treatment;
 (b) fragmenting DNA in the DNA sample to produce fragmented DNA;
 (c) detecting a modified DNA base in the DNA sample according to the method of claim 1 thereby identifying at least one of the location or amount of the modified nucleotide in the DNA sample;
 (d) determining differences in at least one of the location or the amount of the modified nucleotide in the DNA sample in comparison to the location or the amount of the modified base in at least one of (i) one or more reference samples from one or more healthy subjects or (ii) one or more samples from one or more subjects having the disease or condition; and
 (e) indicating that the subject is responding to the treatment if at least one of the location or the amount of the modified nucleotide in the DNA sample is similar to the location, the amount, or both, of the modified base in the one or more reference samples from one or more healthy subjects, or indicating that the subject not responding to the treatment if at least one of the location or the amount of the modified nucleotide in the DNA sample is similar to the location, the amount, or both, of the modified base in the one or more samples from one or more subjects having the disease or condition.

Embodiment 28. The method of embodiment 27, wherein the method is performed at one or more future points in time to monitor the responsiveness of the subject to the treatment over time.

Embodiment 29. The method of embodiment 27 or 28, further comprising performing steps (b) and (c) on a DNA sample obtained from the subject prior to the subject receiving the treatment.

Embodiment 30. The method of embodiment 29, wherein the one or more samples from one or more subjects having the disease or condition is the DNA sample obtained from the subject prior to receiving the treatment.

Embodiment 31. A method of monitoring a subject for accumulation of DNA damage associated with a treatment, comprising:
 (a) providing a first DNA sample from a subject prior to administration of the treatment;
 (b) fragmenting DNA in the first DNA sample to produce fragmented DNA;
 (c) detecting a modified DNA base in the first DNA sample according to the method of claim 1 thereby identifying at least one of the location or amount of the modified nucleotide in the DNA sample;
 (d) providing a second DNA sample from the subject after administration of the treatment;
 (e) fragmenting DNA in the second DNA sample to produce fragmented DNA;
 (f) detecting the modified DNA base in the second DNA sample according to the method of claim 1;
 (g) determining differences in at least one of the location or the amount of the modified nucleotide in the first DNA sample in comparison to the second DNA sample; and
 (h) indicating that the subject has accumulated DNA damage if at least one of the location or the amount of the modified nucleotide in the second DNA sample has increased compared to the first DNA sample, or that the subject has not accumulated DNA damage if at least one of the location or the amount of the modified nucleotide in the second DNA sample is similar to the first DNA sample.

Embodiment 32. The method of embodiment 31, wherein steps (d) to (h) are performed at a future point in time to monitor the accumulation of DNA damage in the subject.

Embodiment 33. The method of embodiment 31 or 32, wherein the treatment is at least one of radiation therapy or chemotherapy.

Embodiment 34. A method of developing a genetic profile for a subject, comprising:
(a) providing a DNA sample from a subject;
(b) fragmenting DNA in the DNA sample to produce fragmented DNA;
(c) incubating a DNA sample comprising fragmented DNA with a plurality DNA glycosylases that excise a plurality of modified nucleotides, each DNA glycosylase excising a different kind of modified nucleotide, to form apurinic or apyrimidinic sites (AP sites) at the sites of the modified nucleotides in the fragmented DNA;
(d) treating the fragmented DNA of step (c) with a DNA polymerase and labeled nucleotides complimentary to nucleotides opposite the AP sites, each kind of labeled nucleotide having a different kind of label, thereby incorporating the labeled nucleotides at the AP site in the fragmented DNA;
(e) isolating the fragmented DNA containing the labeled nucleotides; and
(d) detecting the positions of the labeled nucleotides in the fragmented DNA to determine the location of the modified nucleotides in the DNA sample, quantitating the amounts of labeled nucleotides in the fragmented DNA to determine amount of the modified nucleotides in the DNA sample, or both detecting the positions and quantitating the amounts of the labeled nucleotides in the fragmented DNA to determine the locations and amounts of the modified nucleotide in the DNA sample, thereby generating a genetic profile for the subject.

Embodiment 35. The method of embodiment 34, wherein the DNA sample is incubated with one DNA glycosylase at a time in step (c).

Embodiment 36. The method of embodiment 34, wherein the DNA sample is split into multiple portions in step (c), each portion incubated with a different DNA glycosylase.

Embodiment 37. The method of any one of embodiments 34-36, further comprising performing the method on a DNA sample from the subject at one or more future points in time.

Embodiment 38. A method of determining an environmental exposure time of a biological sample containing DNA, comprising:
(a) providing a DNA sample that has been exposed to an environmental condition;
(b) fragmenting DNA in the DNA sample to produce fragmented DNA;
(c) treating the fragmented DNA with a DNA polymerase and a labeled nucleotide complimentary to a nucleotide opposite the AP site thereby incorporating the labeled nucleotide at the AP site in the fragmented DNA;
(c) isolating the fragmented DNA containing the labeled nucleotide; and
(d) detecting the position of the labeled nucleotide in the fragmented DNA to determine the location of the modified nucleotide in the DNA sample, quantitating the amount of labeled nucleotide in the fragmented DNA to determine amount of the modified nucleotide in the DNA sample, or both; and
(e) comparing the location, the amount, or both, of the modified nucleotide in the DNA sample to a plurality of reference samples that have been exposed to the environmental condition, each reference sample exposed to the environmental condition for a different length of time, wherein the environmental exposure time of the DNA sample is determined by the reference sample having the most similar location, amount, or both, of modified nucleotide as compared to the DNA sample.

II. Kits

In another aspect, kits comprising reagents for performing the methods as described herein are provided. Various enzymes may be included in the kit. In some instances, the kit includes one or more DNA glycosylase. Each DNA glycosylase may have specificity for one or more different kinds of modified bases or one or more types of base modifications. In some instances, the kit also includes an AP endonuclease. In some instances, the kit may also include a DNA polymerase lacking 3'→5' exonuclease activity and strand displacement activity. In some instances, the kit may also include a DNA ligase.

In some instances, the kit may further include one or more labeled nucleotides or, alternatively, may include a label and reagents for adding the label to nucleotides. The labeled nucleotides included in the kit may include labeled dATP, dUTP, dTTP, dCTP, dGTP, and useful modifications thereof. In some instances, only labeled nucleotides that are complementary to the base incorporated opposite the modified base to be excised may be included in the kit; that is the kit may be designed for the detection of specific modified bases. In some instances, the kit may also include one or more canonical (unlabeled) nucleotides.

In some instances, the kit may include enzymes and reagents useful for altering the type of modified base that can be detected using a given DNA glycosylase. For example, the kit may include a modifying enzyme that alters a base such that it is no longer recognized and excised by a DNA glycosylase that typically would do so. In another example the kit may include a modifying enzyme that alters a base such that it is recognized and excised by a DNA glycosylase that typically would not do so. In one example, enzymes and reagents that may be useful for use with thymine DNA glycosylase (TDG) include TET enzyme, β-glucosyltransferase and glucose, or some combination thereof.

In some instances, the kit may include one or more buffers and/or reaction components for performing the excision or labeling steps of the method. For example, the kit may include one or more of a DNA glycosylase buffer, a ligase buffer, a DNA polymerase buffer, or any combination thereof. The kit may also include reagents such as salts, cations, or detergents.

In some instances, the kit includes reagents and instructions for fragmentation of the DNA sample. For example, the kit may include one or more enzymes for fragmenting the DNA. For example, the kit may include any of DNAse I, maltose binding protein-T7 Endo I and a nonspecific nuclease such as *Vibrio vulnificus* nuclease (Vvn), or NEBNext® dsDNA Fragmentase®.

In some instances, the kit may further include control DNA oligonucleotides containing one or more modified bases (for example, different types of modified bases, different base modifications, or both). The control DNA oligonucleotides may be provided in a known concentration and having a known amount of modified base per DNA molecule or concentration. In some instances, the size of the control DNA oligonucleotides may be in a specific size range. In some instances, the control DNA oligonucleotides may be in the range of about 25-100 bp, about 25-150 bp, about 50-200 bp, about 25-200 bp, about 50-250 bp, about 25-250 bp, about 50-300 bp, about 25-300 bp, about 50-500 bp, about 25-500 bp, about 150-250 bp, about 100-500 bp, about 200-800 bp, about 500-1300 bp, about 750-2500 bp, about 1000-2800 bp, about 500-3000 bp, about 800-5000 bp. For example, the control DNA oligonucleotides may be in the range of 25-100 bp, 25-150 bp, 50-200 bp, 25-200 bp, 50-250 bp, 25-250 bp, 50-300 bp, 25-300 bp, 50-500 bp, 25-500 bp, 150-250 bp, 100-500 bp, 200-800 bp, 500-1300 bp, 750-2500 bp, 1000-2800 bp, 500-3000 bp, 800-5000 bp. For example, the control DNA oligonucleotide may be about 50-250 bp. In one example, the size of the control DNA oligonucleotide may be in the range of 50-250 bp. In some instances, the control DNA oligonucleotide may be larger or smaller than any stated range by about 25 bp. In some instances, the control DNA oligonucleotide may be in the same approximate size range as the DNA molecules to be analyzed using the kit. In some instances, the described base excision and labeling reactions may be performed on a DNA sample and the control DNA oligonucleotides in parallel. Analysis of the amount of labeling of the control DNA oligonucleotides may be used to quantitate the amount of label incorporated into the DNA sample and, thus, the amount of a particular modified base in the sample. For example, a standard curve may be generated based on labeling incorporated into a plurality of amounts of a control DNA oligonucleotide, and the amount of labeling incorporated into the DNA sample may be compared to the standard curve to determine the amount of the modified base present in the DNA sample. In another example, the control DNA oligonucleotides may be combined with the isolated labeled DNA at a known amount (spiked in) for quantitation. In some instances, the kit may include a plurality of aliquots of control DNA oligonucleotides, each control DNA oligonucleotide having a known amount of a different modified base.

In some instances, the kit may further include instructions. The instructions may specify how to perform one or more of the DNA isolation step, the DNA fragmentation step, the excision step of the described method, the labeling step of the described method, or labeled DNA isolation step of the described method. Instructions describing how to use control DNA oligonucleotides to quantitate the amount of label incorporated into the DNA sample may be included in the kit.

Non-limiting embodiments include:

Embodiment 39. A kit for detection of a modified nucleotide in a DNA sample, comprising: an enzyme selected from at least one of a DNA glycosylase, an AP endonuclease, a DNA polymerase lacking proofreading and strand displacement activity, or a DNA ligase; and at least one kind of labeled nucleotide.

Embodiment 40. The kit of embodiment 39, further comprising one or more of a buffer for the enzyme, at least one kind of unlabeled nucleotide, or control DNA oligonucleotides comprising a known amount or location pattern of labeled nucleotides.

III. Compositions

In another aspect, provided are DNA oligonucleotides containing one or more modified bases. In some instances, the DNA oligonucleotides contain a modified base. In some instances, the DNA oligonucleotides contain multiple modified bases of the same kind. In some instances, the DNA oligonucleotides contain at least two different types of modified bases (for example, different bases or different base modifications). In some instances, the size of the control DNA oligonucleotides may in a specific size range. For example, the control DNA oligonucleotides may be in the range of about 25-100 bp, about 25-150 bp, about 50-200 bp, about 25-200 bp, about 50-250 bp, about 25-250 bp, about 50-300 bp, about 25-300 bp, about 50-500 bp, about 25-500 bp, about 150-250 bp, about 100-500 bp, about 200-800 bp, about 500-1300 bp, about 750-2500 bp, about 1000-2800 bp, about 500-3000 bp, about 800-5000 bp, or other size range between about 25 bp and 5000 bp. For example, the control DNA oligonucleotides may be in the range of 25-100 bp, 25-150 bp, 50-200 bp, 25-200 bp, 50-250 bp, 25-250 bp, 50-300 bp, 25-300 bp, 50-500 bp, 25-500 bp, 150-250 bp, 100-500 bp, 200-800 bp, 500-1300 bp, 750-2500 bp, 1000-2800 bp, 500-3000 bp, 800-5000 bp, or other size range between 25 bp and 5000 bp. For example, the DNA oligonucleotides may be about 50-250 bp. In one example, the size of the control DNA oligonucleotide may be in the range of 50-250 bp. In some instances, the DNA oligonucleotide may be larger or smaller than any stated range by about 25 bp. In some instances, the DNA oligonucleotides may be useful as control reagents for use in analyzing the amount of labeled nucleotides incorporated into DNA fragments in the described methods. In some instances, the DNA oligonucleotides may be included as control DNA oligonucleotides in the kits described herein. In some instances, the DNA oligonucleotides may be used in the methods described herein as control oligonucleotides to facilitate quantitation of modified bases in a DNA sample. In some instances, the control DNA oligonucleotide may be in the same approximate size range as the DNA molecules to be analyzed using the described kit. In some instances, the described base excision and labeling reactions may be performed on a DNA sample and the control DNA oligonucleotides in parallel. Analysis of the amount of labeling of the control DNA oligonucleotides may be used to quantitate the amount of label incorporated into the DNA sample and, thus, the amount of a particular modified base in the sample. In one example, a standard curve may be generated based on labeling incorporated into a plurality of amounts of a control DNA oligonucleotide, and the amount of labeling incorporated into the DNA sample may be compared to the standard curve to determine the amount of the modified base present in the DNA sample. In another example, the control DNA oligonucleotides may be combined with the isolated labeled DNA at a known amount (spiked in) for quantitation.

Non-limiting embodiments include:

Embodiment 41. A plurality of oligonucleotides, each oligonucleotide comprising a known amount of a modified nucleotide.

Embodiment 42. The mixture of embodiment 41, wherein at least a portion of the oligonucleotides comprise a known amount of a second kind of modified nucleotide.

Embodiment 43. The mixture of embodiment 41 or 42, wherein the mixture of oligonucleotides comprises DNA fragments about 50-250 base pairs in length.

IV. Systems and Devices

In another aspect, provided are devices and systems for performing the above-described methods.

Devices

The system of this disclosure may include devices for automating analysis of DNA samples for modified bases.

In one aspect, provided are analytical devices for automating analysis of DNA samples for modified bases. In another aspect, provided are sample devices configured to receive a DNA sample for analysis of DNA samples. In one example, the sample device may be a microfluidic sample device. For example, the sample device may be a lab-on-a-chip microfluidic device. In some instances, the analytical device is configured to receive one or more sample devices.

In some instances, the analytical device may include a receptacle to receive one or more sample devices, as described below.

In some instances, the analytical device may include a display. The display may be configured to output one or more graphical objects. In some instances, the display may comprise a touch-screen display. The touch-screen display may be configured to detect user interaction with the touch-screen display and transmit one or more associated sensor signals to a processor (for example, internal to the analytical device). The sensor signal may comprise data associated with the user interaction, such as a location, direction, and/or pressure of the user interaction.

The analytical device may additionally or alternatively comprise a user input device. The user input device may comprise a touch-screen display; a touch pad; a keypad; one or more buttons, knobs, or switches; or any combination of any of such user input devices. The user input device may be configured to receive user input and transmit an associated sensor signal to a processor.

In some cases, the analytical device may further comprise a computing device. For example, the computing device may comprise a memory and a processor. The memory may comprise any suitable tangible (and non-transitory) computer-readable medium such as RAM, ROM, EEPROM, or the like, and may embody program components that configure operation of the analytical device. In some instances, the memory may comprise software instructions configured to cause the processor to execute one or more functions. For example, the software instructions may be configured to cause the processor to coordinate the injection of reagents at specific time points into one or more chambers or compartments of a sample device located within the analytical device. For example, the software instructions may include a timed and/or sequential addition of reagents to one or more sample devices contained within the analytical device. In another example the software instruction may cause timed and/or sequential physical, mechanical, or electrochemical adjustment to one or more sample devices contained within the analytical device. In some instances, the memory may comprise software instructions configured to perform any of the methods described throughout this disclosure.

In some cases, the analytical device may comprise a network interface. The network interface may comprise any components that facilitate a network connection or otherwise facilitate communication between devices. Examples include, but are not limited to, wired interfaces such as Ethernet, USB, IEEE 1394, and/or wireless interfaces such as IEEE 802.11, Bluetooth, near-field communication (NFC) interfaces, RFID interfaces, or radio interfaces for accessing cellular telephone networks (e.g., transceiver/antenna for accessing a CDMA, GSM, UMTS, or other mobile communications network). The analytical device may use the network interface to receive or transmit information about the DNA sample to a remote device.

In some instances, the analytical device is configured to receive a sample device within which one or more steps of the described methods are performed.

In one aspect, provided are sample devices within which one or more steps of the described methods may be performed. An exemplary sample device is shown in FIG. 7, which includes a first solid surface, a second solid surface in contact with the first solid surface, an inlet, a first chamber, a second chamber, a third chamber, an outlet, a buffer compartment, an outlet, and a plurality of channels connecting the various components to each other. The sample device may have an inlet into which sample DNA is introduced.

In some instances, the sample device includes a first solid surface and a second solid surface in contact with the first solid surface. The first and second solid surface may have various geometric shapes such as, for example, a square shape, a rectangle shape, a circular shape, an oval shape, a triangle shape, or some other shape. In some instances, the shape of the solid substrates may be varied. For example, one portion of a solid surface may be rectangular and another portion may have a different shape. A sample device may include first and second solid substrates that are the same shape or different shapes from each other. The dimensions of the solid substrates may be governed by the desired overall configuration of the sample device. In some cases, the first and second solid surfaces may have substantially the same dimensions.

In some instances, the inlet is formed in the first solid surface, the second solid surface, or a junction between the first and second solid surface. The sample device may further include a plurality of chambers and channels. The sample device may have a plurality of chambers containing one or more reagents for performing the steps of the described methods. The chambers and channels may all be formed in the first solid surface or the second solid surface, or some chambers and channels may be formed in the first solid surface and other chambers and channels may be formed in the second solid surface.

In one example, the first chamber (1) may contain lyophilized DNA glycosylase. The DNA sample may move from the inlet to the first chamber via a first channel and be incubated there to allow the DNA glycosylase to excise the modified nucleotide of interest. Chamber (1) may further contain an AP endonuclease. Alternatively, the sample device may include a separate chamber (not shown) containing a lyophilized AP endonuclease. The DNA sample may move from the first chamber to the AP endonuclease chamber via a side channel and be incubated there to allow the endonuclease to generate gaps in the DNA sample at the location of the AP sites.

In some instances, the sample device may further include a second chamber (2) that contains an affinity component for the DNA sample. The DNA sample may move from the first chamber, or the AP endonuclease chamber, into the second chamber via a second channel. The second chamber may contain an affinity component, such as silica beads or ion exchange beads to which the DNA sample binds. The sample device may also include channels connecting the second chamber to a wash buffer compartment and/or elution buffer compartment. The DNA sample bound to the the affinity component may be washed by wash buffer introduced into the second chamber from the wash buffer compartment and eluted from the affinity component by elution buffer introduced into the second chamber from the elution buffer compartment. In some instances, the channels connecting the wash buffer compartment and/or elution buffer compartment to the second chamber may have valves (grey X squares) that permit controlled introduction of buffers into the second chamber.

In some instances, the eluted DNA sample may move from the second chamber to the third chamber via a third channel. The third channel may contain lyophilized DNA polymerase and labeled nucleotides. In some instances, the DNA sample is maintained in the third chamber to permit incorporation of label nucleotides into the gaps present in the DNA sample. In some instances, the labeled DNA sample may then be ejected from the sample device through an outlet.

In other instances, the sample device may further include a purification chamber (not shown) connected to the third chamber via a purification channel (not shown). The purification chamber may be configured similar to the second chamber. The purification chamber may contain an affinity component to which the labeled DNA sample binds and may be connected to a wash buffer compartment and/or elution buffer compartment via side channels. The DNA sample bound to the affinity component may be washed by wash buffer introduced into the second chamber from the wash buffer compartment and eluted from the affinity component by elution buffer introduced into the second chamber from the elution buffer compartment. In some instances, the channels connecting the wash buffer compartment and/or elution buffer compartment to the second chamber may have valves (grey X squares) that permit controlled introduction of buffers into the second chamber. For example, where the label is biotin, the purification channel may contain streptavidin-coated beads, and the elution buffer may be formulated to facilitate elution of the biotin-labeled DNA sample from the streptavidin-coated beads. In some instances, the labeled DNA sample may then be ejected from the sample device through an outlet.

In some instances, the sample device may further include a detection chamber (not shown) connected to the third chamber (or to the purification chamber mentioned in the previous paragraph) via a detection channel (not shown). The detection chamber may be configured to contain reagents for detection of the label incorporated into the DNA sample. The detection chamber may be configured to permit quantitation of the amount of one or more labels incorporated into the DNA sample.

In some instances, the sample device may have other configurations to include chambers in which other enzymatic reactions may take place. For example, the sample device may include a plurality of chambers each containing a different DNA glycosylase. The sample device may split a sample into separate portions, or have a plurality of inlets, to permit incubation of the DNA sample with the plurality of DNA glycosylases at the same time. In another example, the sample device may include a plurality of chambers each containing a different DNA glycosylase that are arrayed within the sample device such that the DNA sample moves sequentially from one to another. In some instances, additional affinity chambers, wash buffer compartments, and elution buffer components are included permit washing of the DNA sample and removal of reagents from a preceding chamber before the sample moves into a next chamber. In another example, the sample device may contain chambers containing enzymes and reagents to modify the modified bases detected by the DNA glycosylase as described above. In some instances, the various chambers and compartments of the sample device are connected via channels. In some instances, the channels contain valves that control the access of fluids within one chamber or compartment to another chamber or compartment.

In some instances, the sample devices may include an identification component to facilitate identification of a sample device. In some instances, the identification component may include information about the DNA sample contained within the sample device. For example, the identification component may be a unique serial number that can be associated with the DNA sample. In another example, the identification component is a location on the sample device on which a user may write information about the DNA sample or the method to be performed thereon. In another example, the identification component may be a memory component or memory device on which may be stored information such as, but not limited to, the identity of the source of the DNA sample, other information about the DNA sample, and the method to be performed on the DNA sample.

In some instances, the described sample devices may be made from various materials. Generally, the materials are non-reactive to nucleic acids and do not substantially bind to nucleic acids, proteins, nucleotides, or the label used for the labeled nucleotides. Exemplary materials include, but are not limited to, polypropylene, siliconized polypropylene, and glass and polydimethylsiloxane functionalized (coated) with polyethylene glycol, POP-6™ polymer (Life Technologies, Inc.), or other blocking layers.

A non-limiting embodiment includes:

Embodiment 44. A sample device for detection of a modified nucleotide in a DNA sample, comprising:

a solid surface;

a second solid surface in contact with the first solid surface;

an inlet; and at least one chamber connected to the inlet and configured to perform at least one of (i) a base excision reaction, (ii) a DNA labeling reaction, (iii) isolation of labeled DNA, or (iv) at least one of DNA detection, quantitation, or sequencing.

Systems

In one aspect, provided are systems useful for assessing the presence of modified bases in DNA samples. The system includes various components. As used herein, the term "component" is broadly defined and includes any suitable apparatus or collections of apparatuses suitable for carrying out the recited method. The components need not be integrally connected or situated with respect to each other in any particular way. Embodiments include any suitable arrangements of the components with respect to each other. For example, the components need not be in the same room. But in some instances, the components are connected to each other in an integral unit. In some instances, the same components may perform multiple functions.

The system may include an analytical device as described herein. The system may be configured such that the various components of the system transmit or receive information from the analytical device. For example, the system may be configured to receive information from the analytical device as received from a user input device such as, for example, a touch-screen display. The system, such as via the processor, may be configured to receive one or more associated sensor signals transmitted from the analytical device such as, for example, from the user input device. The system may be configured such that the processor of the analytical device transmits and/or receives information from other components of the system.

The system may also include one or more sample devices as described herein. The system may be configured to detect one or more identification component of the sample devices such that the system can distinguish one sample device from another.

The system may comprise one or more computing devices. Typical examples of computing devices include a general-purpose computer, a printer, a programmed microprocessor, a microcontroller, a peripheral integrated circuit element, and other devices or arrangements of devices that are capable of implementing the steps that constitute the method of the present technique.

The computing device comprises a memory. The memory may include random access memory (RAM) and read only memory (ROM), as well as removable media devices, memory cards, flash cards, etc. The computing device may further comprise a storage device. The computing device also comprises a processor. The processor executes a set of instructions that are stored in one or more storage elements (for example, memory or storage device), in order to process input data. In some embodiments, the computing device may comprise a single processor. In other embodiments, the computing device comprises two or more processors. The storage elements may also hold data or other information as desired. The storage elements may be in the form of an information source or a physical memory element present in the processing machine.

A computing device typically will include an operating system that provides executable program instructions for the general administration and operation of that computing device, and typically will include a computer-readable storage medium (for example, a hard disk, random access memory, read only memory, etc.) storing instructions that, when executed by the processor, allow the computing device to perform its intended functions. Suitable implementations for the operating system and general functionality of the computing device are known or commercially available, and are readily implemented by persons having ordinary skill in the art, particularly in light of the disclosure herein The processor is connected to a communication bus. The communication bus may be connected to one or more other components, for example, the processor, an input device (for example, a mouse, keyboard, controller, touch screen, or keypad), and an output device (for example, a display, printer, or speaker). The communication bus may also be connected to the analytical device.

The computing device can also include network components. The network components allow the computing device to connect to one or more networks and/or other databases (for example, database) through an I/O interface. The network components may comprise a network interface. In some embodiments, the network interface is configured for communicating via wired or wireless communication links.

Computing device can also include a computer-readable storage media reader. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. Storage media and computer readable media for containing code, or portions of code, can include any appropriate media known or used in the art.

In some embodiments, the system may execute one or more applications. The one or more applications may be executed on any number of computing devices as described above. For example, the system may execute an application configured to activate a protocol for the analytical device. Such protocol may include a timed, sequential addition of reagents, or adjustment to one or more sample devices contained with the analytical device. The system may also execute an application configured to query the database. In some embodiments, the system may transmit a test result report. In some embodiments, the system may transmit the test report to a computing device. In some embodiments, the system may transmit the test result report to one or more recipients. In some embodiments, the recipient may be the subject or a healthcare provider. In some embodiments, the system may transmit the test result report via e-mail (e.g., to an e-mail account associated with the subject's healthcare provider), SMS, or text message. In some embodiments, the system may store the test result report in the database. Further, the system may provide an electronic notification to a computing device. The computing device may be associated with a healthcare provider, which may be associated with the subject. In some embodiments, the electronic notification may comprise an e-mail, a text message, or a push notification. The electronic notification may indicate that a test report is available, for example, for download from the database.

A non-limiting embodiment includes:

Embodiment 45. An analytical device, for detection of a modified nucleotide in a DNA sample, comprising:

a receptacle configured to receive one or more sample devices according to embodiment 44; and a user input device; and a computing device comprising a memory and a processor, the memory comprising software instructions configured to cause the processor to execute one or more functions to perform at least one of (i) a base excision reaction, (ii) a DNA labeling reaction, (iii) isolation of labeled DNA, or (iv) at least one of DNA detection, quantitation, or sequencing.

EXAMPLES

The following examples are offered to illustrate, but not to limit, the claimed invention.

Example 1

A study was performed to identify DNA polymerase properties useful for labeling methylated or damaged nucleotide bases in genetic sequences. Of specific interest was whether the labeling reaction could be improved by using a DNA polymerase that lacked 3'→5' proofreading exonuclease activity. It was hypothesized that 3'→5' exonuclease activity could result in excision of incorporated labeled bases, which would reduce the efficiency of the labeling reaction. Such exonuclease activity could also result in excision of additional nucleoside bases in the 5' direction from the excised base. Because the polymerase is supplied with only one (biotin-conjugated) nucleoside, this is most likely to cause the polymerase to either (i) pause permanently at a base 5' from the target, resulting in no label incorporation, or (ii) incorporate a labeled nucleoside at a site 5' from the targeted modified base, leaving a gap and misidentifying the position of the modified base. As such, using a DNA polymerase lacking 3'→5' exonuclease activity was proposed to increase the efficiency of the labeling reaction. To test this hypothesis, an experiment was conducted to compare wild type T4 DNA polymerase (WT T4 pol; New England Biolabs) and mutated T4 DNA polymerase lacking 3'→5' exonuclease activity (T4 pol exo⁻; Lucigen, 1 U/20 pmol DNA).

Figure 1:
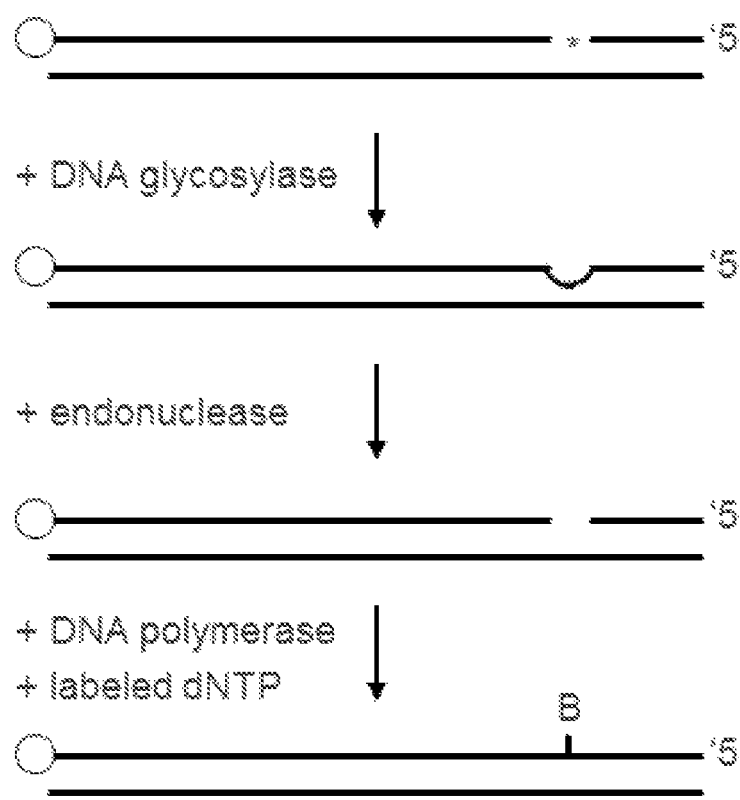
FIG. 1 depicts a schematic showing the steps of labeling a DNA molecule containing a modified base of interest according to aspects of the disclosure. A modified base (*)

Two 40 base pair complementary DNA molecules were ordered from Integrated DNA Technologies and annealed together by mixing together at a 1:1 ratio, heating to 95° C., and cooling slowly over ~1 hr to form a double-stranded DNA construct as shown schematically in FIG. 1. One strand of the DNA construct contained a 3' fluorescein amidite (FAM) label and a uracil at base position 34. No other uracil bases were present in the construct.

In a first step, ~4 µg of the DNA construct was co-incubated with uracil DNA glycosylase (New England Biolabs, 1 U/400 ng DNA) and Endonuclease IV (New England Biolabs, 1 U/200 ng DNA) in a buffer containing 50 mM Tris-HCl, 100 mM NaCl, 10 mM $MgCl_2$, and 1 mM DTT (total vol=50 µL) for 1 hour at 37° C. The glycosylase creates an abasic site by cleaving the uracil base from the construct, and the endonuclease cleaves both 3' and 5' to the site, resulting in a 33 base pair strand and a 6 base pair fragment annealed to the full length 40 base pair complement strand (lane 1 in each image). Resulting DNA was purified using a commercial kit (Qiagen).

In a second step, the purified DNA construct was treated with biotinylated dUTP (Life Technologies, 15 pmol) and either T4 pol exo⁻ or WT T4 pol (20 U/pmol DNA) for 1 hour at 37° C. in buffer containing 10 mM Tris-HCl (pH 7.9), 10 mM MgCl$_2$, 50 mM NaCl, and 1 mM DTT. In this step, the DNA polymerases will incorporate the biotinylated dUTP into the FAM-labeled strand opposite to an adenine base in the complementary strand.

The final reaction products were run on denaturing sequencing gels (16% gel matrix, 0.09% APS, 0.06% TEMED, run in 3X TBE) and imaged at 520 nm to detect FAM emission. Exemplary gel images are shown in FIG. 2. Only products containing the 3' FAM label are detectable. Each lane contains approximately 40 ng total DNA.

The left side lane of each gel image shows the intermediate reaction products following the first step described above. Both gels show the 33 nucleotide FAM-labeled molecule. The right side lane of each gel image shows the final reaction products following the second step described above.

The reaction using WT T4 pol resulted in the desired 34 nucleotide product into which a single biotinylated dUTP was incorporated at the position of the excised uracil base, but also resulted in several degradation products arising from cleaving of nucleosides from the FAM-labeled strand by the 5'→5' exonuclease activity of the WT T4 pol. Without being held to any particular theory, it is proposed that these unwanted labeled products includes both paused extensions and misincorporation of biotinylated uracils at positions of adenine bases on the complementary strand. As a result, the total yield of desired 34 nucleotide band is at most 20-25% of the total DNA.

In contrast, the reaction using T4 pol exo⁻ resulted primarily in the desired 34 nucleotide product into which a single biotinylated dUTP was incorporated at the position of the excised uracil base, with a total yield of about 89%.

The conclusion from this study is that the efficiency and accuracy of the labeling reaction is substantially increased by using a DNA polymerase that lacks 3'→5' exonuclease activity.

Example 2

A study was performed to identify DNA polymerase concentrations useful for labeling methylated or damaged nucleotide bases in genetic sequences. Of specific interest was whether the labeling reaction could be improved by limiting the availability of DNA polymerase. This is because excess polymerase concentration can have spurious effects, including elevated error rates (misincorporation), untemplated incorporation, and interference that can lower activity, while too limited availability can result in low yield (that is a lot of unlabeled DNA). To test this hypothesis, a titration experiment assessing various DNA polymerase concentrations was performed.

The same DNA construct as described in Example 1 was used for this study. Excision of the uracil base was also performed as described in Example 1 on a total of about 50 μg of DNA construct. The resulting material was purified using a commercial kit (Qiagen), suspended in 10 mM Tris-HCl, pH 8.5 and divided into 13 aliquots containing approximately 2 μg of DNA construct. Each aliquot received 15 pmol biotinylated dUTP (Life Technologies) and T4 pol exo⁻ (Lucigen) at various concentrations as described in Table 2 below. The reaction conditions were 1 hour at 37° C. in buffer containing 10 mM Tris-HCl (pH 7.9), 10 mM MgCl$_2$, 50 mM NaCl, and 1 mM DTT.

TABLE 2

| | DNA polymerase titration in labeling reaction. | | |
|---|---|---|---|
| Lane | DNA pol/DNA construct (U/mol) | DNA pol Dilution | DNA pol (mU) |
| 1 | — | — | — |
| 2 | — | — | — |
| 3 | 1 U/nmol | 1X | 78.5 |
| 4 | 500 U/pmol | ½ | 39.2 |
| 5 | 250 U/pmol | ¼ | 19.6 |
| 6 | 125 U/pmol | ⅛ | 9.8 |
| 7 | 66.7 U/pmol | 1/15 | 5.2 |
| 8 | 50 U/pmol | 1/20 | 3.9 |
| 9 | 33.3 U/pmol | 1/30 | 2.6 |
| 10 | 20 U/pmol | 1/50 | 1.6 |
| 11 | 10 U/pmol | 1/100 | 0.78 |
| 12 | 5 U/pmol | 1/200 | 0.39 |
| 13 | 1 U/pmol | 1/500 | 0.16 |

Analysis was performed on a denaturing sequencing gel (16% gel matrix, 0.09% APS, 0.06% TEMED, run in 3:1 1×TBE) imaged for FAM labeled DNA. Exemplary gel images are shown in FIG. 3. Each lane contains 20 ng total DNA. Lane 1 shows the migration pattern of the full length 40 nucleotide FAM-labeled strand; lane 2 shows the migration pattern of the intermediate 33 nucleotide FAM-labeled strand following the uracil excision step.

Reactions conducted using high DNA polymerase concentrations yield variable activity including excess incorporation—that is, incorporation of one or more non-complementary biotinylated-dUTP into the FAM-labeled strand as reflected by the higher/larger bands—and missed material—that is, FAM-labeled strands that were not extended by addition of any biotinylated-dUTP as reflected by the lower/smaller bands. Reactions conducted using very low concentration of DNA polymerase resulted in significant reduction in yield of the desired 34 nucleotide product into which a single biotinylated dUTP was incorporated at the position of the excised uracil base. A maximum yield of the desired product, with minimal amounts of unwanted products, was about 89% of the desired product out of total DNA. This was observed with a DNA polymerase concentration of about 20 U/ pmol DNA.

The conclusion from this study is that the efficiency and accuracy of the labeling reaction is substantially increased by using a limited amount of DNA polymerase in the range of about 10-30 U/pmol.

Example 3

Using the conditions worked out in Examples 1 and 2, the detection method of the disclosure was used to specifically excise and label uracil, oxoguanine, and T:G mismatches. Three DNA constructs were prepared, each construct containing a single uracil, oxoguanine, or T:G mismatch. FIG. 4A shows the migration patterns of each DNA construct (left lane of each gel). The glycosylase and endonuclease pairings were: (1) uracil: UDG and Endo VI; (2) oxoguanine: hOOG1 and Endo IV; and (3) T:G mismatch: TDG and Endo IV. All samples were first treated with glycosylase and endonuclease and then purified by column filtration prior to the polymerase step. The TDG reaction product is treated with proteinase K following TDG incubation and purified by column filtration prior to subsequent endonuclease and polymerase steps, requiring an additional purification step relative to UDG and hOGG1. Co-incubation of the DNA constructs with the respective glycosylase/endonuclease pairing resulted in cleavage of the target base and generation of an abasic site. The shortened product is shown in FIG. 4A (middle lane of each gel). Biotinylated dUTP, dGTP, and dCTP were incorporated into the abasic sites using DNA polymerase as described above, resulting in incorporation of the labeled bases into the respective DNA molecules (right lane of each gel in FIG. 4A). As UDG and TDG are both monofunctional glycosylases, and hOGG1 is a bifunctional glycosylase, this experiment demonstrates the applicability of the described method to all classes of DNA glycosylases.

As specific cleavage of target DNA modifications is important to insure accurate and reliable labeling in a DNA molecule, the specificity of several DNA glycosylases was assessed.

In one experiment, a DNA construct containing a single oxoG modification was prepared. The construct was incubated in parallel with UDG, hOOG1, and TDG (co-incubated with Endo IV). As shown in FIG. 4B, only hOGG1 was able to excise the oxoG from the DNA construct as reflected by the altered migration pattern for that reaction product as compared to the starting DNA construct. In contrast, the products from the cleavage reactions with UDG and TDG have the same migration pattern as the starting material, showing that they did not nonspecifically excise the oxoG from the DNA construct.

In another experiment, UDG, TDG, and hOGG1 were assessed to determine if they showed any cleavage for DNA modifications other than their known specificity. UDG is known to excise uracil modifications, TDG is known to excise T:G mismatches, and hOGG1 is known to excise oxoG modifications. Three DNA construct were prepared: one containing a single uracil modification, one containing a single oxoG modification, and one containing a single T:G mismatch. Aliquots of each DNA construct were separately incubated with two DNA glycosylases that have specificity for a different type of modification than present in the DNA construct. Specifically, the uracil DNA construct was incubated with hOGG1 or TDG; the oxoG construct was incubated with UDG or TDG; and the T:G mismatch construct was incubated with UDG or hOGG1. In each instance, the DNA construct was co-incubated with the DNA glycosylase and Endo IV. For the TDG reactions, a proteinase K treatment was performed to degrade bound TDG and material was purified by column filtration prior to Endo IV incubation. As shown in FIG. 4C, none of the DNA glycosylases cleaved the modification present in the tested DNA molecules, demonstrating the specificity of the glycosylases for their target modifications. Thus, a given DNA glycosylase can be used in the described method to specifically excise and label a specific DNA modification and mislabeling of other types of modifications in the same reaction should be minimal or nonexistent.

Example 4

The utility and efficiency of the excision and labeling reactions were also assessed in a one-pot set up. UDG and EndoIV were co-incubated with a 40 nt DNA molecule having a single uracil modification in buffer containing 50 mM NaCl, 10 mM Tris-HCl, 10 mM $MgCl_2$, 1 mM DTT, pH 7.9. After incubation for the excision reaction, an aliquot was taken for later analysis. Then T4 DNA pol exo⁻ and biotinylated dUTP were added for the labeling reaction. The 40 nt DNA molecule, the mid-point sample, and the end product were run on a denaturing gel. As shown in FIG. 5, the uracil was efficiently cleaved from the 40 nt molecule as shown by the faster migration pattern of the DNA in the mid-point sample (middle lane) and, importantly, incorporation of the biotinylated dUTP into the DNA molecule was also efficient as shown by the slower migration pattern (right lane; marked with *). Similar results were obtained using hOGG1, Endo IV, and a DNA molecule containing an oxoG modification. Yield is higher in a one-pot reaction (~95%) than in the multi-step process while requiring a total incubation of only one hour and no intermediate purification steps.

Example 5

An example method for targeting multiple DNA modifications by tailoring the selectivity of the DNA glycosylases are provided and illustrated in FIG. 6A and FIG. 6B. A DNA sample is shown that contains carboxycytosine (caC) and formylcytosine (fC) (white circle), methylcytosine (mC, black circle), and hydroxymethylcytosine (hmC, square) genetic modifications. Thymine DNA glycosylase (TDG) has selectivity for caC and fC.

As shown in FIG. 6A, TDG glycosylase can be used to identify mC and hmC if, after the excision step (as described in Example 1) is performed, the target DNA is further treated with additional enzymes to introduce modifications. For simplicity, the following discussion will make reference to biotinylated dCTP (triangle) as the labeled nucleotide. However, it is understood that other labeling methods and other nucleotides can be used depending on the glycosylase used and the detection method of interest.

Reaction route (1) shows an example method for the identification of caC/fC modifications in the target DNA. TDG glycosylase can be used to excise the caC/fC, and the labeling reaction can be performed using biotinylated dCTP to label only positions where the caC/fC was present. This reaction route permits identification of caC/fC modifications in the target DNA.

Reaction route (2) shows an example method for the identification of mC and hmC in the target DNA. First, TDG glycosylase can be used to excise the caC/fC and gap filling can be performed with canonical dCTP. Then TET enzyme may be used to demethylate and convert both mC and hmC to caC/fC. Then, TDG glycosylase can be used to excise the caC/fC, and the labeling reaction can be performed using biotinylated dCTP, which will be incorporated into positions where mC and hmC had been present in the target DNA.

Reaction route (3) shows an example method for the identification of mC in the target DNA. TDG glycosylase can be used to excise the caC/fC and gap filling can be performed with canonical dCTP. Then β-glucosyltransferase can be used to selectively attach a glucose moiety to hmC. Treatment of the target DNA with TET enzyme will then demethylate and convert only mC to caC/fC. The labeling reaction can be performed using biotinylated dCTP, which will be incorporated into positions where mC had been present in the target DNA. Subtraction of the mC target population from the mc+hmC target population will identify the target population containing hmC only.

FIG. 6B shows another means of specifically labeling and detecting caC, fC, mC, and hmC in a DNA sample using TDG and uracil DNA glycosylase (UDG).

Reaction route (1) shows the example method to detect fC/caC as described above.

Reaction route (2) shows an example method to detect hmC. First, TDG glycosylase can be used to excise the caC/fC and gap filling can be performed with canonical dCTP. KRuO$_4$ can be used to oxidize hmC to caC/fC, which can then be cleaved by TDG, thereby labeling the site of hmC in the DNA sample with labeled dCTP (for example, biotinylated dCTP).

Reaction route (3) shows an example method to detect mC. TDG glycosylase can be used to excise the caC/fC and gap filling can be performed with canonical dCTP. β-glucosyltransferase can be used to selectively attach a glucose moiety to hmC, thereby blocking it from oxidation. Then either APOBEC3a or bisulfite can convert mC to uracil, which can then be cleaved by UDG and labeled with labeled dCTP (for example, biotinylated dCTP).

All patents, patent publications, patent applications, journal articles, books, technical references, and the like discussed in the instant disclosure are incorporated herein by reference in their entirety for all purposes.

It is to be understood that the figures and descriptions of the invention have been simplified to illustrate elements that are relevant for a clear understanding of the invention. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of this disclosure.

What is claimed:

1. A method of detecting a modified DNA base in a DNA sample, comprising:
   (a) incubating a DNA sample comprising fragmented DNA with a DNA glycosylase that excises a modified nucleotide to form an apurinic or apyrimidinic site (AP site) at the site of the modified nucleotide in the fragmented DNA;
   (b) treating the fragmented DNA of step (a) with a DNA polymerase and a labeled nucleotide complimentary to a nucleotide opposite the AP site thereby incorporating the labeled nucleotide at the AP site in the fragmented DNA;
   (c) isolating the fragmented DNA containing the labeled nucleotide; and
   (d) (i) detecting the position of the labeled nucleotide in the fragmented DNA to determine the location of the modified nucleotide in the DNA sample, (ii) quantitating the amount of labeled nucleotide in the fragmented DNA to determine amount of the modified nucleotide in the DNA sample, or (iii) both detecting the position and quantitating the amount of the labeled nucleotide in the fragmented DNA to determine the location and amount of the modified nucleotide in the DNA sample.

2. The method of claim 1, wherein the DNA sample is genomic DNA, mitochondrial DNA, or a combination thereof.

3. The method of claim 1, wherein the DNA sample comprises DNA fragments about 50-250 base pairs in length.

4. The method of claim 1, where in the modified nucleotide is at least one of methylcytosine (mC), hydroxymethylcytosine (hmC), carboxycytosine (caC), formylcytosine (fC), 8-oxo-7,8-dihyroguanine (8-oxoG), uracil, methyladenine(mA), 8-oxoadenine, O6-methylguanine, 1-methyladenine, O4-methylthymine, 5-hydroxycytosine, 5-hydroxyuracil, 5-hydroxymethyluracil, or thymine dimers.

5. The method of claim 1, wherein the DNA glycosylase is at least one of uracil DNA glycosylase (UDG), methyl-binding domain glycosylase 4 (MBD4), thymine DNA glycosylase (TDG), 8-oxoguanine DNA glycosylase (OGG), FaPy-DNA glycosylase (FPG), MutY homolog DNA glycosylase (MYH/MUTYH), methylpurine DNA glycosylase (MPG), endonuclease III-like DNA glycosylase 1 (NTHL1), endonuclease VIII-like DNA glycosylase 1 (NEIL1), endonuclease VIII-like DNA glycosylase 2 (NEIL2), endonuclease VIII-like DNA glycosylase 3 (NEIL3), T4 pyrimidine dimer DNA glycosylase (T4 PDG), T4 endonuclease V, Mug-DNA glycosylase (MUG), alkyl adenine DNA glycosylase (AAG), SMUG DNA glycosylase (SMUG), endonuclease III, and endonuclease VIII.

6. The method of claim 1, further comprising incubating the fragmented DNA of step (a) with an AP endonuclease before performing step (b).

7. The method of claim 1, wherein the DNA polymerase does not have 3'→5' exonuclease activity or strand displacement activity.

8. The method of claim 1, wherein the DNA polymerase may be is a mutated T4 DNA polymerase lacking 3'→5' exonuclease activity.

9. The method of claim 1, wherein the amount of DNA polymerase used in step (b) may be about 10 U/pmol to about 30 U/pmol total DNA.

10. The method of claim 1, wherein the labeled nucleotide is biotin-labeled nucleotide.

11. The method of claim 1, wherein isolating the fragmented DNA containing the labeled nucleotide comprises contacting the fragmented DNA with streptavidin attached to a solid support and removing fragmented DNA not bound thereto when the labeled nucleotide is biotin-labeled nucleotide.

12. The method of claim 1, wherein step (d) comprises quantitating the amount of labeled nucleotides in the fragmented DNA, and the method further comprises comparing the amount of labeled nucleotides to the amount of labeled nucleotides in a reference sample containing a known amount of labeled nucleotides.

13. The method of claim 1, wherein detecting the position of the labeled nucleotide comprises sequencing the isolated fragmented DNA.

* * * * *